United States Patent [19]
Koga et al.

[11] Patent Number: 5,658,888
[45] Date of Patent: Aug. 19, 1997

[54] ERYTHROMYCIN DERIVATIVES

[75] Inventors: Hiroshi Koga; Tsutomu Sato; Hisanori Takanashi, all of Shizuoka, Japan

[73] Assignee: Chugai Seiyaku Kabushiki Kaisha, Tokyo, Japan

[21] Appl. No.: 318,814

[22] PCT Filed: May 26, 1993

[86] PCT No.: PCT/JP93/00702

§ 371 Date: Oct. 19, 1994

§ 102(e) Date: Oct. 19, 1994

[87] PCT Pub. No.: WO93/24509

PCT Pub. Date: Dec. 9, 1993

[30] Foreign Application Priority Data

May 26, 1992 [JP] Japan ...................... 4-133828

[51] Int. Cl.$^6$ ................ A61K 31/70; C07M 17/08
[52] U.S. Cl. .................. 514/29; 536/7.2; 536/7.3; 536/7.4
[58] Field of Search ............ 536/7.2, 7.3, 7.4; 514/29

[56] References Cited

U.S. PATENT DOCUMENTS 4,677,097  6/1987  Omura et al. .................. 514/29

FOREIGN PATENT DOCUMENTS

| 0213617 | 3/1987 | European Pat. Off. . |
| 0215355 | 3/1987 | European Pat. Off. . |
| 60-218321 | 11/1985 | Japan . |
| 61-87625 | 5/1986 | Japan . |
| 9313780 | 7/1993 | WIPO . |

OTHER PUBLICATIONS

Omura et al., "Macrolides with Gastrointestinal Motor Stimulating Activity", *Journal of Medicinal Chemistry*, vol. 30, No. 11, pp. 1941–1943, Nov. 1987.
*Therapeutic Research*, vol. 11, No. 11, pp. 58(3548)–69(3559), 1990.
Sunazuka et al, *Mortilides, Macrolides with Gastrointestinal Motor Stimulating Activity. II. Quaternary N–Substituted Derivatives of 8,9–Anhydroerythromycin A 6,9–Hemiacetal and 9,9–Dihydroerythromycin A 6,9–Epoxide*, Chem. Phar. Bull., vol. 37 No. 10, pp. 2701–2709, 1989.
Tsuzuki et al, *Motilides, Macrolides with Gastrointestinal Motor Stimulating Activity. I.O–Substituted and Tertiary N–Substituted Derivatives of 8,9–Anhydroerythromycin A 6,9–Hemiacetal*, Chem. Pharm. Bull., vol. 37, No. 10, pp. 2687–2700, Oct. 1989.

Primary Examiner—Elli Peselev
Attorney, Agent, or Firm—Browdy and Neimark

[57] ABSTRACT

Compounds represented by the general formula:

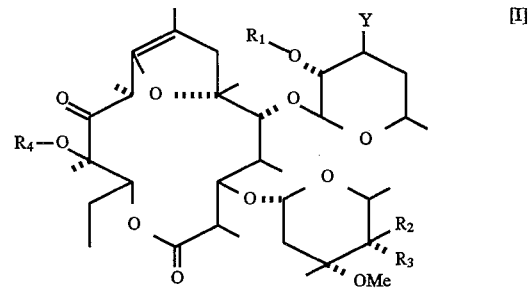

wherein $R_1$ is a hydrogen atom or an acyl group;

$R_2$ and $R_3$ may be the same or different, and each represents a hydrogen atom, hydroxyl group, acyloxy group or amino group, or, in combination, they represent $=O$ or $=NOR_{10}$, where $R_{10}$ represents a hydrogen atom or lower alkyl group;

$R_4$ represents a hydrogen atom or lower alkyl group; and

Y represents $-NR_5R_6$ or $-N^+R_7R_8R_9X^-$, where $R_5$, $R_6$, $R_7$, $R_8$ and $R_9$ may be the same or different, and each represents a hydrogen atom or an unsubstituted or substituted lower alkyl group, lower alkenyl group, lower alkinyl group, cycloalkyl group or 3–7-membered heterocyclic group comprising an oxygen atom, nitrogen atom or sulphur atom as an heteroatom, and X represents an anion, where $R_5$ and $R_6$, or $R_7$ and $R_8$ may form an azacycloalkyl group together with the neighboring nitrogen atom, respectively, and salts thereof.

These compounds and their salts are subject to a remarkably lower degree of decomposition by gastric acid than are the publicly known erythromycin derivatives of the prior art, and have an excellent enterolinesis stimulating action.

22 Claims, No Drawings

1

ERYTHROMYCIN DERIVATIVES

FIELD OF THE INVENTION

The present invention relates to erythromycin derivatives and their salts which act to stimulate the contractile motility of alimentary canals of mammals, and are thus useful as stimulants for the contractile mobility of alimentary canals.

DESCRIPTION OF THE PRIOR ART

On the basis of differences in their mechanisms, prokinetic agents are roughly classified into 4 groups: direct cholinergic drugs such as aclatonium napadisilate; indirect cholinergic drugs such as cisapride; dopamine blockers such as domperidone; and opiate agonists such as trimebutine maleate, and are widely used as therapeutic agents for dysfunction of enterokinesis, particularly for symptoms of digestive organs such as, for example, gastrointestinal complaints due to hypokinesia. However, these drugs have adverse effects such as extrapyramidal symptoms or stimulation of prolactin release caused by the dopamine blocking action. In addition, it is known that the action of these drugs, which is different from that of a spontaneous, physiological movement propagating from the upper gastrointestinal tract to the lower gastrointestinal tract, often leads to the onset of adverse effects such as fluor, emesis or the like.

On the other hand, motilin is known as a gastrointestinal hormone which stimulates the contractile motility of alimentary canals, but its supply by extraction of natural sources or by chemical synthesis has not been satisfactory, and thus a large supply thereof has been difficult to secure. Further, motilin is a peptide consisting of 22 amino acids, so the development of an oral preparation comprising it has been difficult.

In recent years, erythromycin and its derivatives have been found to have a powerful stimulating activity with respect to the contractile motility of alimentary canals, and EM-523, one of the derivatives, is being developed as a prokinetic agent (Japanese Patent Application Disclosure SHO No. 60-218321, Japanese Patent Application Disclosure SHO No. 61-87625, Japanese Patent Application Disclosure SHO No. 63-99016, Japanese Patent Application Disclosure SHO No. 63-99092 and The Journal of Pharmacology and Experimental Therapeutics, vol. 251, No. 2, pp. 707–712, 1989).

EM-523 is, however, unstable in the presence of an acid, and therefore it is supposed that its action diminishes due to the decomposition thereof by gastric acid when used via oral administration. In view of these facts, we the present inventors have conducted research in order to find erythromycin derivatives which are acid resistant and capable of being administered orally, and as a result, we have found that the non-documented novel erythromycin derivatives described hereunder have such properties and action as mentioned above, thus eventually completing the present invention based on this finding.

DISCLOSURE OF THE INVENTION

That is, the present invention relates to the compounds represented by the following formula (I):

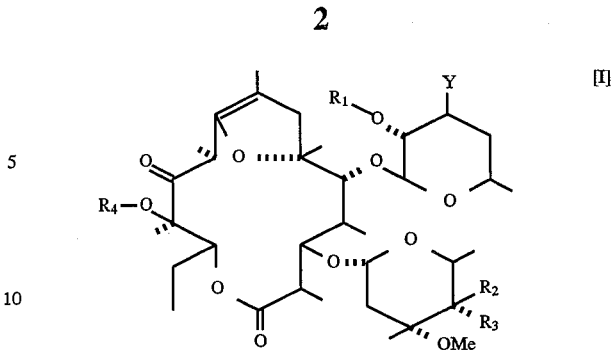

wherein $R_1$ is a hydrogen atom or an acyl group;

$R_2$ and $R_3$ may be the same or different, and each represents a hydrogen atom, hydroxyl group, acyloxy group or amino group, or, in combination, they represent =O or =NOR$_{10}$, where $R_{10}$ represents a hydrogen atom or lower alkyl group;

$R_4$ represents a hydrogen atom or lower alkyl group; and

Y represents —NR$_5$R$_6$ or —N$^+$R$_7$R$_8$R$_9$X$^-$, where $R_5$, $R_6$, $R_7$, $R_8$ and $R_9$ may be the same or different, and each represents a hydrogen atom or an unsubstituted or substituted lower alkyl group, lower alkenyl group, lower alkynyl group, cycloalkyl group or 3–7-membered heterocyclic group comprising an oxygen atom, nitrogen atom or sulphur atom as an heteroatom, and X represents an anion, where $R_5$ and $R_6$, or $R_7$ and $R_8$ may form an azacycloalkyl group together with the neighboring nitrogen atom, respectively, and salts thereof.

Throughout the specification and the claims, the acyl group means formyl group, acetyl group, propionyl group, butyryl group, pivaloyl group, benzoyl group, ethoxycarbonyl group, t-butoxycarbonyl group, benzyloxycarbonyl group, etc.; the acyloxy group means formyloxy group, acetyloxy group, propionyloxy group, butyryloxy group, pivaloyloxy group, benzoyloxy group, ethoxycarbonyloxy group, t-butoxycarbonyloxy group, benzyloxycarbonyloxy group, etc.; the lower alkyl group means straight or branched alkyl group of 1–6 carbon atoms, and preferably includes methyl group, ethyl group, n-propyl group, i-propyl group, n-butyl group, i-butyl group, sec-butyl group, t-butyl group, neopentyl group, etc.; the lower alkenyl group means straight or branched alkenyl group of 2–6 carbon atoms, and preferably includes vinyl group, allyl group, n-butenyl group, i-butenyl group and sec-butenyl group; and the lower alkynyl group means straight or branched alkynyl group of 2–6 carbon atoms, and preferably includes ethynyl group, propargyl group and butynyl group, etc.

The azacycloalkyl group means cycloalkyl group with one or more carbon atoms thereof replaced by nitrogen atoms, and includes, for example, an aziridinyl group, azetidinyl group, pyrrolidinyl group, piperidinyl group, hexamethyleneimino group, etc. The cycloalkyl group means a cycloalkyl group of 3–8 carbon atoms, and preferably includes a cyclobutyl group, cyclopentyl group, cyclohexyl group, etc. Examples of the heterocycle of the 3–7-membered heterocyclic group comprising an oxygen atom, nitrogen atom or sulphur atom as the heteroatom include, for example, aziridine, azetidine, pyrrolidine, piperidine, oxirane, oxetane, oxolane, tetrahydropyran, thiirane, thietane, thiolane, thiane, etc. Illustrative examples of the substituent on the unsubstituted or substituted lower alkyl group, lower alkenyl group, lower alkinyl group, cycloalkyl group or 3–7-membered heterocyclic group comprising an oxygen atom, nitrogen atom or sulphur atom as an heteroatom includes a hydroxy group, amino group, halogen atom, cyano group, alkyloxy group, mercapto group, acyl group, carbamoyl group, etc. and additional illustrative examples of the substituent on the cycloalkyl group or 3–7-membered fumaric heterocyclic group comprising an oxygen atom, nitrogen atom or sulphur atom as an heteroatom include a hydrocarbon group such as a lower alkyl group, lower alkenyl group, lower alkynyl group, aryl group, aralkyl group and the like.

The anion includes a chloride ion, bromide ion, iodide ion, carboxylate ion, sulfonate ion, etc. The acid available for use for the formation of the salts includes an inorganic acid such as hydrochloric acid, hydrobromic acid, hydriodic acid, sulfuric acid or the like, or an organic acid such as acetic acid, oxalic acid, maleic acid, fumaric acid, succinic acid, methanesulfonic acid or the like.

BEST MODE FOR CARRYING OUT THE INVENTION

The compounds (I) according to the present invention may be prepared by, for example, subjecting a compound (II) to an oxidation reaction, and, if necessary, further to alkylation and deprotection.

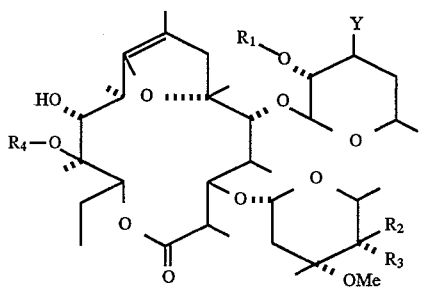

wherein $R_1$, $R_2$, $R_3$, $R_4$ and Y have the same meanings as stated above.

The oxidant available for use in the above mentioned oxidation reaction includes a metallic oxidant such as chromic acid; manganese oxide or the like, or an oxidant utilizing an organic compound such as dimethylsulfoxide or the like. The alkylation may be carried out in the presence or absence of a base, by the action of an alkylating agent such as an alkyl halide, acrylic acid derivative or the like in an inert solvent. The base available for use includes, for example, a metal base such as sodium hydride, sodium alkoxide, potassium alkoxide, alkyl lithium, potassium carbonate, sodium carbonate, sodium bicarbonate, potassium hydroxide or sodium hydroxide, or an organic base such as triethylamine, trimethylamine, diisopropylethylamine or pyridine. The inert solvent available for use includes methanol, ethanol, propanol, chloroform, methylene chloride, ether, tetrahydrofuran, N,N-dimethylformamide and so on. The alkyl group of the alkyl halide means a carbon chain of 1–6 carbon atoms which may be branched and may comprise an unsaturated bond or a substituent such as a hydroxyl group, amino group, halogen atom, cyano group, alkyloxy group, mercapto group, formyl group or the like, and as the alkyl halide may be employed a chloride, bromide or iodide comprising the alkyl group as defined above, while acrylic acid, an acrylic ester, acrylonitrile, acrolein or the like may be employed as the acrylic acid derivative.

In view of the facts as evidenced in the experiments that the compounds (I) of the present invention did not undergo a decrease in their activity under acidic conditions, which is different from the case of EM-523, and demonstrated a powerful enterokinesis stimulating action when orally administered, the compounds are useful particularly as contractile motility stimulants for alimentary canals of mammals.

A detailed explanation will be made hereunder regarding the preparation of the compounds according to the present invention, with reference to the Examples, to which the present invention is, however, not limited in any way.

EXAMPLE 1

To a solution of a mixture of 25 g of 2'-O-acetyl-4"-O-formyl-8,9-anhydroerythromycin A 6,9-hemiketal (Compound 1) [Literature: J. Tadanier, et al., Journal of Organic Chemistry, 39,2495 (1974)], 24.6 ml of dimethylsulfoxide and 19.7 g of dicyclohexylcarbodiimide in 400 ml of methylene chloride was added 18.4 g of pyridinium trifluoroacetate while cooling with ice. The resulting mixture was stirred at room temperature for 4 hours, after which the insoluble matter was filtered off. The filtrate was washed with water, dried over anhydrous sodium sulfate, and then the solvent was distilled off. The resulting residue was purified by silica gel column chromatography [developing solvent: chloroform-methanol-conc. aqueous ammonia (30:1:0.1)] to yield 18.8 g (yield: 67%) of 2'-O-acetyl-4"-O-formyl-11-oxo-8,9anhydroerythromycin A 6,9-hemiketal (Compound 2) as a white powder.

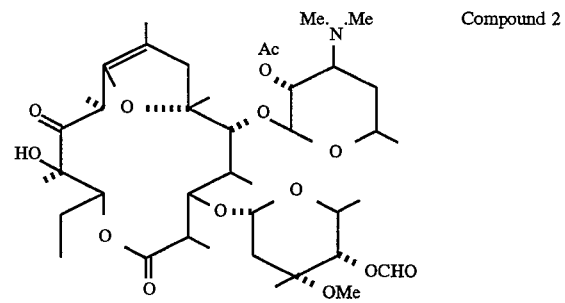

Compound 2

EXAMPLE 2

To a solution of Compound 2 (15.8 g) in 300 ml of N,N-dimethylformamide under cooling with ice and stirring, were added 1.20 g of 60% sodium hydride and then, after stirring for 20 minutes, 2.5 ml of methyl iodide. The mixture was stirred for 2 hours, followed by addition of a saturated aqueous sodium bicarbonate and extraction with ethyl acetate. The organic layer was washed with water and saturated saline, dried over anhydrous sodium sulfate, and thereafter the solvent was distilled off. The resulting residue was dissolved in 150 ml of methanol, and 10 ml of a saturated aqueous sodium bicarbonate was added to the solution which was then stirred at room temperature overnight. The reaction solution was extracted with chloroform, washed with saturated saline, dried over anhydrous sodium sulfate, and the solvent was distilled off. The resulting residue was purified by silica gel column chromatography [developing solvent: chloroform-methanol-conc. aqueous ammonia (60:1:0.1)] to yield 7.4 g (yield: 51%) of 12-O-methyl-11-oxo-8,9-anhydroerythromycin A 6,9-hemiketal (Compound 3) as a white powder.

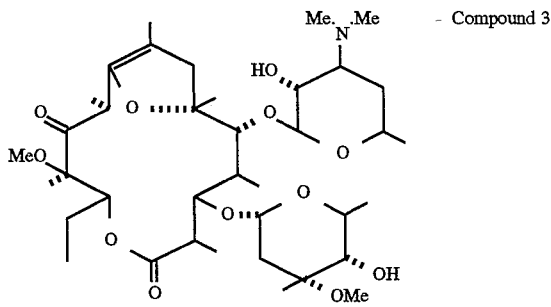

Compound 3

EXAMPLE 3

A solution of Compound 3 (6.9 g) and 3.9 g of sodium acetate in 90 ml of 80% methanol/water was heated to 50° C., and, while stirring, 3.6 g of iodine was added to the solution. The mixture was stirred at that temperature for 2 hours while keeping its pH at 8-9 by addition of an appropriate amount of 1N aqueous solution of sodium hydroxide. The reaction solution was poured into 350 ml of water which contained 7 ml of conc. aqueous ammonia, extracted with chloroform, dried over anhydrous sodium sulfate, and thereafter the solvent was distilled off. The resulting residue was purified by silica gel column chromatography [developing solvent: chloroform-methanol-conc. aqueous ammonia (40:1:0.1)] to yield 5.21 g (yield: 77%) of de(N-methyl)-12-O-methyl-11-oxo-8,9-anhydroerythromycin A 6,9-hemiketal (Compound 4) as a white powder.

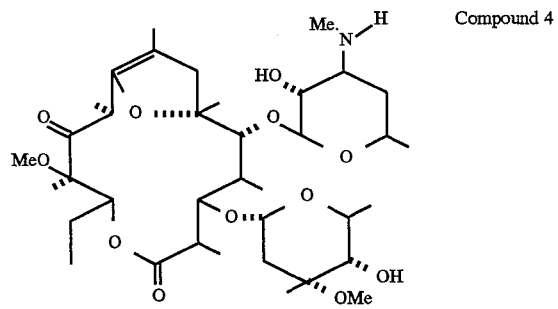

Compound 4

EXAMPLE 4

To a solution of Compound 4 (160 mg) in 5 ml of methanol were added 290 mg of di-isopropylethylamine and 1.4 g of ethyl iodide, followed by stirring at 40° C. for 20 hours. After the solvent was distilled off, the reaction solution was diluted with chloroform and washed with water and a saturated saline. The chloroform solution was dried over anhydrous sodium sulfate, and the solvent was distilled off. The resulting residue was purified by silica gel column chromatography [developing solvent: chloroform-methanol-conc. aqueous ammonia (80:1:0.1)] to yield 105 mg (yield: 63%) of ethyl-nor-12-O-methyl-11-oxo-8,9-anhydroerythromycin A 6,9-hemiketal (Compound 5) as a white powder.

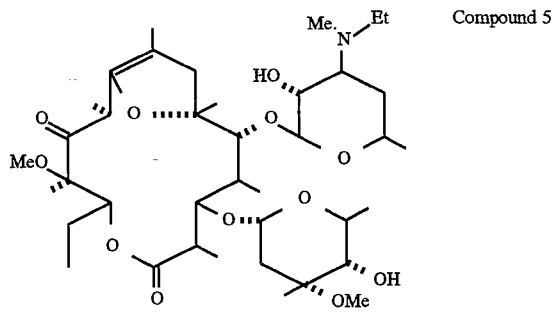

Compound 5

EXAMPLE 5

To a solution of Compound 4 (485 mg) in 10 ml of methanol were added 877 mg of di-isopropylethylamine and 4.62 g of isopropyl iodide, followed by stirring at 60° C. for 5 days. After the solvent was distilled off, the reaction solution was diluted with chloroform and washed with water and a saturated saline. The chloroform solution was dried over anhydrous sodium sulfate, and the solvent was distilled off. The resulting residue was purified by silica gel column chromatography [developing solvent:chloroform-methanol-conc. aqueous ammonia (100:1:0.1)] to yield 262 mg (yield: 50%) of isopropyl-nor-12-O-methyl-11-oxo-8,9-anhydroerythromycin A 6,9-hemiketal (Compound 6) as a white powder.

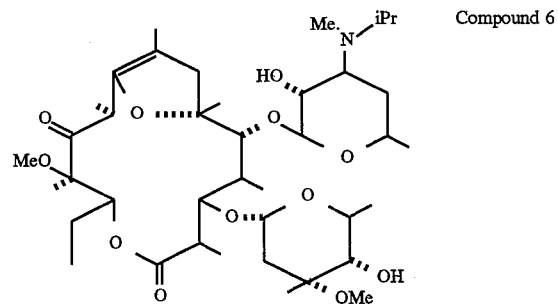

Compound 6

EXAMPLE 6

To a solution of Compound 4 (250 mg) in 4 ml of methanol were added 453 mg of di-isopropylethylamine and 2.38 g of 1-iodopropane, followed by stirring at 50° C. for 1 day. After the solvent was distilled off, the reaction solution was diluted with chloroform and washed with water and a saturated saline. The chloroform solution was dried over anhydrous sodium sulfate, and the solvent was distilled off. The resulting residue was purified by silica gel column chromatography [developing solvent: chloroform-methanol-conc. aqueous ammonia (150:1:0.1)] to yield 170 mg (yield: 64%) of propyl-nor-12-O-methyl-11-oxo-8,9-anhydroerythromycin A 6,9-hemiketal (Compound 7) as a white powder.

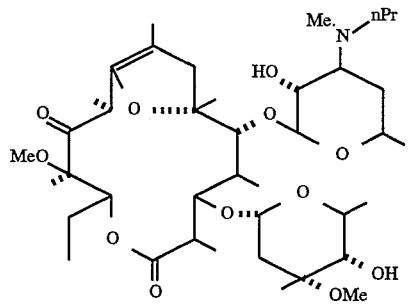

EXAMPLE 7

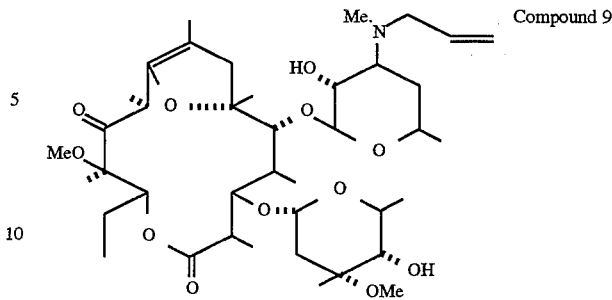

EXAMPLE 9

To a solution of Compound 4 (250 mg) in 4 ml of methanol were added 59 mg of sodium bicarbonate and 0.050 ml of allyl bromide, followed by stirring at 40° C. overnight. After the solvent was distilled off, the reaction solution was diluted with chloroform and washed with water and a saturated saline. The chloroform solution was dried over anhydrous sodium sulfate, and the solvent was distilled off. The resulting residue was purified by silica gel column chromatography [developing solvent: chloroform-methanol-conc. aqueous ammonia (150:1:0.1)] to yield 156 mg (yield: 59%) of allyl-nor-12-O-methyl-11-oxo-8,9-anhydroerythromycin A 6,9-hemiketal (Compound 8) as a white powder.

To a solution of Compound 4 (250 mg) in 4 ml of methanol were added 453 mg of di-isopropylethylamine and 1.41 g of 4-bromo-1-butene, followed by stirring at 50° C. for 1 day. After the solvent was distilled off, the reaction solution was diluted with chloroform and washed with water and a saturated saline. The chloroform solution was dried over anhydrous sodium sulfate, and the solvent was distilled off. The resulting residue was purified by silica gel column chromatography [developing solvent: chloroform-methanol-conc. aqueous ammonia (150:1:0.1)] to yield 152 mg (yield: 56%) of 3-butenyl-nor-12-O-methyl-11-oxo-8,9-anhydroerythromycin A 6,9-hemiketal (Compound 10) as a white powder.

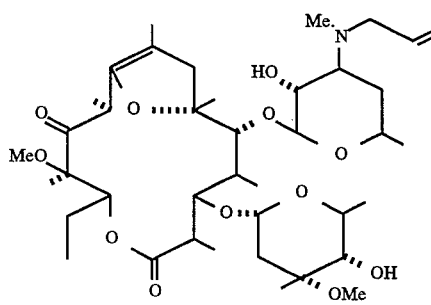

EXAMPLE 8

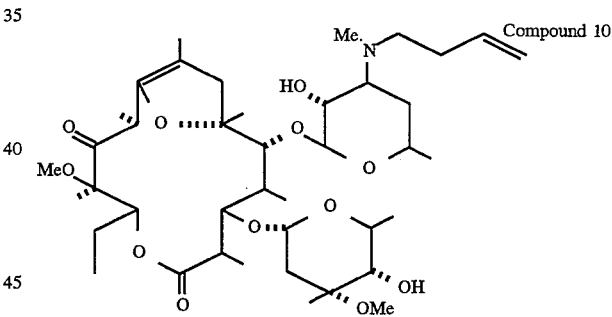

EXAMPLE 10

To a solution of Compound 4 (250 mg) in 4 ml of methanol were added 59 mg of sodium bicarbonate and 0.034 ml of propargyl bromide, followed by stirring at 50° C. for 2 hours. After the solvent was distilled off, the reaction solution was diluted with chloroform and washed with water and a saturated saline. The chloroform solution was dried over anhydrous sodium sulfate, and the solvent was distilled off. The resulting residue was purified by silica gel column chromatography [developing solvent: chloroform-methanol-conc. aqueous ammonia (150:1:0.1)] to yield 105 mg (yield: 40%) of propargyl-nor-12-O-methyl-11-oxo-8,9-anhydroerythromycin A 6,9-hemiketal (Compound 9) as a white powder.

To a solution of Compound 4 (250 mg) in 4 ml of methanol were added 453 mg of di-isopropylethylamine and 1.75 g of bromoethanol, followed by stirring at 50° C. for 1 day. After the solvent was distilled off, the reaction solution was diluted with chloroform and washed with water and a saturated saline. The chloroform solution was dried over anhydrous sodium sulfate, and the solvent was distilled off. The resulting residue was purified by silica gel column chromatography [developing solvent: chloroform-methanol-conc. aqueous ammonia (80:1:0.1)] to yield 205 mg (yield: 77%) of 2-hydroxyethyl-nor-12-O-methyl-11-oxo-8,9-anhydroerythromycin A 6,9-hemiketal (Compound 11) as a white powder.

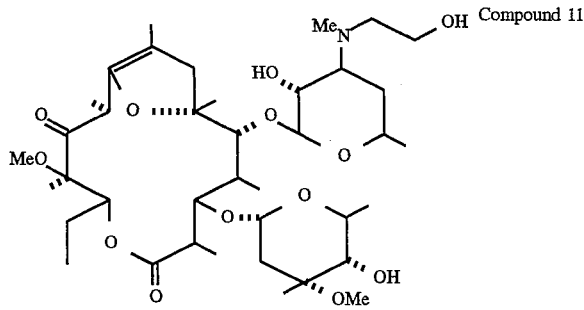

Compound 11

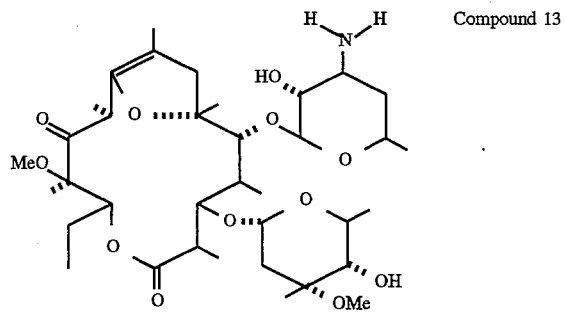

Compound 13

EXAMPLE 11

A solution of Compound 4 (270 mg) in 3 ml of acrylonitrile was heated to reflux for 3 hours. After the solvent was distilled off, the reaction solution was diluted with chloroform and washed with a saturated aqueous sodium bicarbonate and a saturated saline. The chloroform solution was dried over anhydrous sodium sulfate, and the solvent was distilled off. The resulting residue was purified by silica gel column chromatography [developing solvent: chloroform-methanol-conc. aqueous ammonia (200:1:0.1)] to yield 189 mg (yield: 65%) of 2-cyanoethyl-nor-12-O-methyl-11-oxo-8,9-anhydroerythromycin A 6,9-hemiketal (Compound 12) as a white powder.

EXAMPLE 13

To a solution of Compound 13 (700 mg) in 10 ml of methanol were added 388 mg of sodium bicarbonate and 3.1 g of ethyl iodide, followed by stirring at 50° C. for 6 hours. After the solvent was distilled off, the reaction solution was diluted with chloroform and washed with water and a saturated saline. The chloroform solution was dried over anhydrous sodium sulfate, and the solvent was distilled off. The resulting residue was purified by silica gel column column chromatography [developing solvent: chloroform-methanol-conc. aqueous ammonia (120:1:0.1)] to yield 74 mg (yield: 10%) of diethyl-dinor-12-O-methyl-11-oxo-8,9-anhydroerythromycin A 6,9-hemiketal (Compound 14) as a white powder and 172 mg (yield: 24%) of ethyl-dinor-12-O-methyl-11-oxo-8,9-anhydroerythromycin A 6,9-hemiketal (Compound 15) as a white powder.

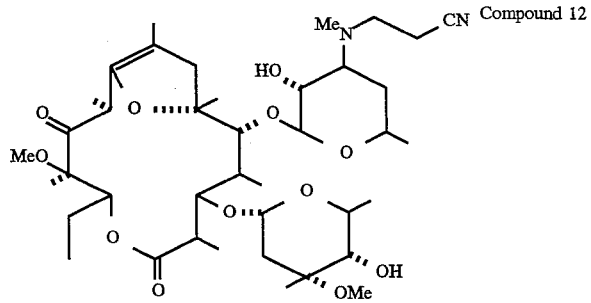

Compound 12

EXAMPLE 12

Seventy-five milliliters of dry methanol was placed in a reactor, and the air therein was evacuated with nitrogen for 20 minutes. Then, 161 mg of metal sodium was added to the solution which started to be cooled with ice at the time the sodium dissolved therein. Thereafter Compound 4 (1.0 g) and then 1.78 g of iodine were added to the mixture. It was stirred for 4 hours in an atmosphere of nitrogen gas while stirring. The reaction solution was poured into 300 ml of water to which 3.0 g of sodium thiosulfate and 2.5 ml of conc. aqueous ammonia had been added. The mixture was extracted with chloroform, washed with a saturated saline, dried over anhydrous sodium sulfate, and the solvent was distilled off. The resulting residue was purified by silica gel column chromatography [developing solvent: chloroform-methanol-conc. aqueous ammonia (50:1:0.1)] to yield 890 mg (yield: 90%) of bis-[de(N-methyl)]-12-O-methyl-11-oxo-8,9-anhydroerythromycin A 6,9-hemiketal (Compound 13) as a white powder.

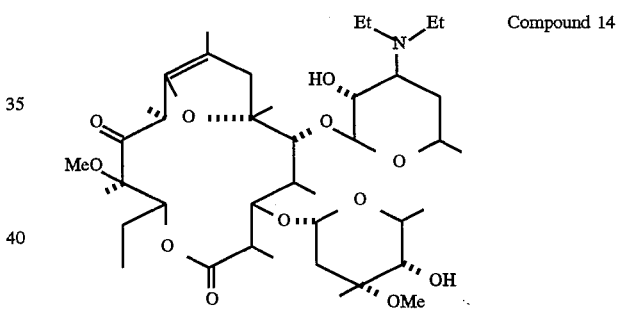

Compound 14

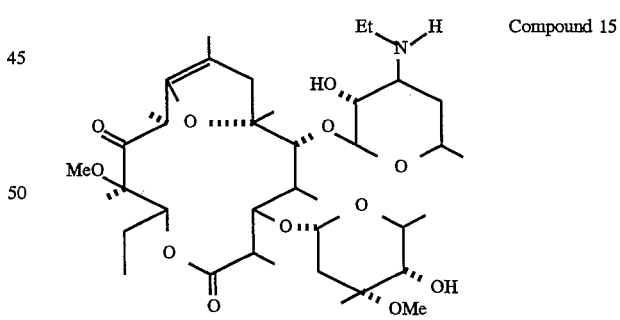

Compound 15

EXAMPLE 14

To a solution of Compound 13 (995 mg) in 20 ml of methanol were added 3.67 g of di-isopropylethylamine and 1.72 g of allyl bromide, followed by stirring at 50° C. for 10 hours. After the solvent was distilled off, the reaction solution was diluted with chloroform and washed with water and a saturated saline. The chloroform solution was dried over anhydrous sodium sulfate, and the solvent was distilled off. The resulting residue was purified by silica gel column chromatography [developing solvent: chloroform-methanol-conc. aqueous ammonia (200:1:0.1)] to yield 490 mg (yield:

44%) of diallyl-dinor-12-O-methyl-11-oxo-8,9-anhydroerythromycin A 6,9-hemiketal (Compound 16) as a white powder.

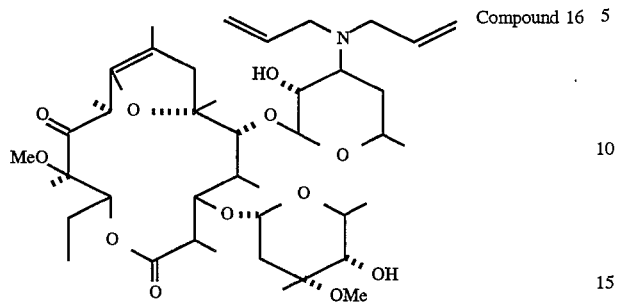

Compound 16

EXAMPLE 15

To a solution of Compound 13 (440 mg) in 10 ml of methanol were added 158 mg of sodium bicarbonate and 0.11 ml of allyl bromide, followed by stirring at 50° C. for 8 hours. After the solvent was distilled off, the reaction solution was diluted with chloroform and washed with water and a saturated saline. The chloroform solution was dried over anhydrous sodium sulfate, and the solvent was distilled off. The resulting residue was purified by silica gel column chromatography [developing solvent: chloroform-methanol-conc. aqueous ammonia (100:1:0.1)] to yield 80 mg (yield: 17%) of allyl-dinor-12-O-methyl-11-oxo-8,9-anhydroerythromycin A 6,9-hemiketal (Compound 17) as a white powder.

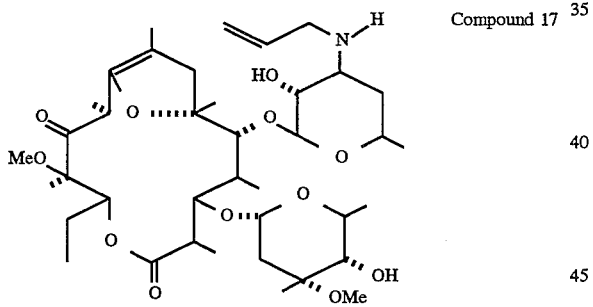

Compound 17

EXAMPLE 16

A solution of Compound 6 (180 mg) and 98 mg of sodium acetate in 3 ml of 80% methanol/water was heated to 50° C., and, while stirring, 91 mg of iodine was added to the solution. The mixture was stirred at that temperature for 2 hours while keeping its pH at 8–9 by addition of an appropriate amount of 1N aqueous solution of sodium hydroxide. The reaction solution was poured into 20 ml of water which contained 1 ml of conc. aqueous ammonia, extracted with chloroform, dried over anhydrous sodium sulfate, and thereafter the solvent was distilled off. The resulting residue was purified by silica gel column chromatography [developing solvent: chloroform-methanol-conc. aqueous ammonia (80:1:0.1)] to yield 70 mg (yield: 40%) of isopropyl-dinor-12-O-methyl-11-oxo-8,9-anhydroerythromycin A 6,9-hemiketal (Compound 18) as a white powder.

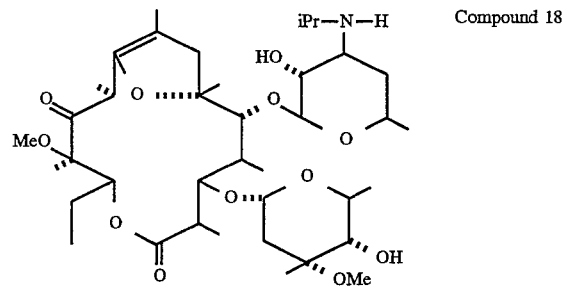

Compound 18

EXAMPLE 17

To a solution of Compound 3 (250 mg) in 3 ml of chloroform was added 0.096 ml of methyl iodide, and the mixture was stirred at room temperature for 4 hours. After the solvent was distilled off, ether was added to the residue to provide a precipitate which was filtered off. The precipitate was washed with ether and dried to yield 206 mg (yield: 69%) of 12-O-methyl-11-oxo-8,9-anhydroerythromycin A 6,9-hemiketal methyl iodide (Compound 19) as a white powder.

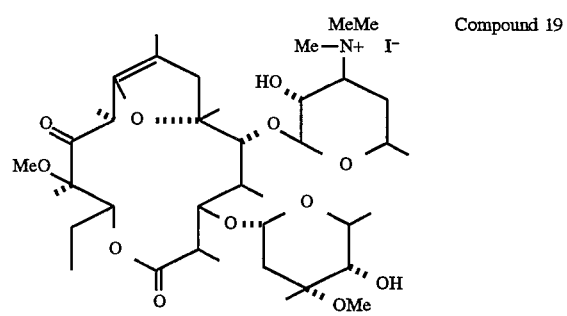

Compound 19

EXAMPLE 18

To a solution of Compound 3 (250 mg) in 3 ml of chloroform was added 0.21 ml of propargyl bromide, and the mixture was stirred at room temperature for 6 hours. After the solvent was distilled off, ether was added to the residue to provide a precipitate which was filtered off. The precipitate was washed with ether and then purified by silica gel column chromatography [developing ,solvent: chloroform-methanol-conc. aqueous ammonia (10:1:0.1)] to yield 198 mg (yield: 68%) of 12-O-methyl-11-oxo-8,9-anhydroerythromycin A 6,9-hemiketal propargyl bromide (Compound 20) as a white powder.

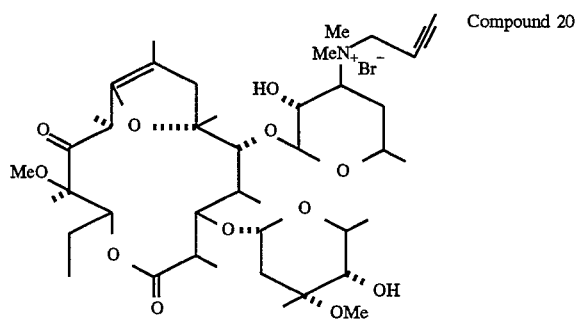

Compound 20

EXAMPLE 19

To a solution of Compound 3 (694 mg) in 10 ml of chloroform under cooling with ice and stirring, were added 0.30 ml of pyridine and then 0.30 ml of acetic anhydride. The mixture was stirred while cooling with ice for 15 minutes, and then at room temperature for 1 hour, followed by addition of a saturated aqueous sodium bicarbonate and extraction with chloroform. The chloroform solution was washed with saturated saline, dried over anhydrous sodium sulfate, and thereafter the solvent was distilled off. The resulting residue was mixed with 0.73 ml of dimethylsulfoxide and 588 mg of di-cyclohexylcarbodiimide, and the mixture was dissolved in 10 ml of methylene chloride, followed by addition of 550 mg of pyridinium fluoroacetate to the resulting solution while cooling with ice. The solution was stirred at room temperature for 4 hours, and the insoluble matter was filtered off. The filtrate was washed with water, dried over anhydrous sodium sulfate, and the solvent was distilled off. The resulting residue was purified by silica gel column chromatography [developing solvent: chloroform-methanol-conc. aqueous ammonia (200:1:0.1)] to yield 428 mg (yield: 58%) of 2'-O-acetyl-12-O-methyl-4",11-dioxo-8,9-anhydroerythromycin A 6,9-hemiketal (Compound 21) as a white powder.

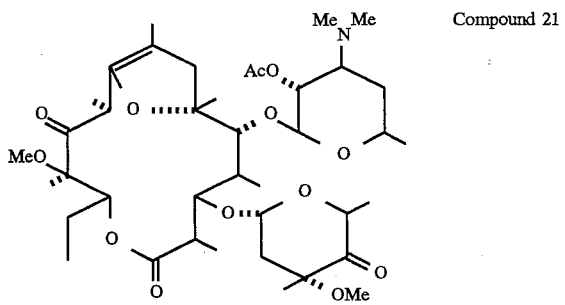

Compound 21

EXAMPLE 20

A solution of Compound 21 (383 mg) in 5 ml of methanol was stirred at room temperature for 20 hours. After the solvent was distilled off, the resulting residue was purified by silica gel column chromatography [developing solvent: chloroform-methanol-conc. aqueous ammonia (200:1:0.1)] to yield 294 mg (yield: 81%) of 12-O-methyl-4",11-dioxo-8,9-anhydroerythromycin A 6,9-hemiketal (Compound 22) as a white powder.

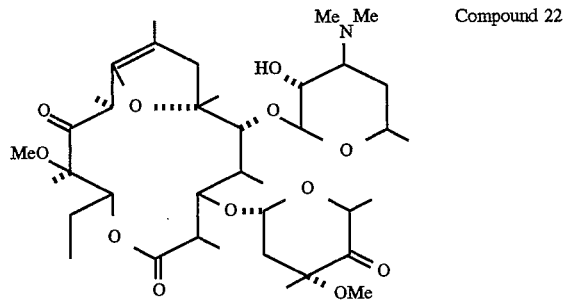

Compound 22

EXAMPLE 21

To a solution of Compound 2 (2.15 g) in 30 ml of methanol was added 8 ml of a saturated aqueous sodium bicarbonate, followed by stirring at room temperature overnight. The reaction solution was extracted with chloroform, washed with a saturated saline and dried over anhydrous sodium sulfate, and the solvent was distilled off. The resulting residue was purified by silica gel column chromatography [developing solvent: chloroform-methanol-conc. aqueous ammonia (70:1:0.1)] to yield 1.84 g (yield: 93%) of 11-oxo-8,9-anhydroerythromycin A 6,9-hemiketal (Compound 23) as a white powder.

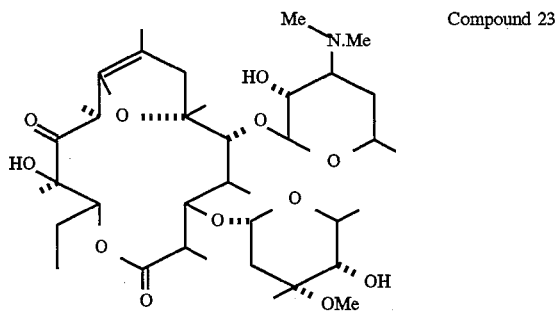

Compound 23

EXAMPLE 22

A solution of Compound 23 (656 mg) and 377 mg of sodium acetate in 10 ml of 804 methanol/water was heated to 50° C., and, while stirring, 350 mg of iodine was added to the solution. The mixture was stirred at that temperature for 2 hours while keeping its pH at 8–9 by addition of an appropriate amount of 1N aqueous solution of sodium hydroxide. The reaction solution was poured into 50 ml of water which contained 3 ml of conc. aqueous ammonia, extracted with chloroform, dried over anhydrous sodium sulfate, and thereafter the solvent was distilled off. The resulting residue was purified by silica gel column chromatography [developing solvent: chloroform-methanol-conc. aqueous ammonia (30:1:0.1)] to yield 428 mg (yield: 66%) of de(N-methyl)-11-oxo-8,9-anhydroerythromycin A 6,9-hemiketal (Compound 24) as a white powder. FAB-MS:m/z 701 (MH$^+$).

To a solution of Compound 24 (205 mg) in 5 ml of methanol were added 378 mg of di-isopropylethylamine and 1.83 g of ethyl iodide, followed by stirring at 40° C. for 20 hours. After the solvent was distilled off, the reaction solution was diluted with chloroform and washed with water and a saturated saline: The chloroform solution was dried over anhydrous sodium sulfate, and the solvent was distilled off. The resulting residue was purified by silica gel column chromatography [developing solvent: chloroform-methanol-conc. aqueous ammonia (60:1:0.1)] to yield 139 mg (yield:65%) of ethyl-nor-11-oxo-8,9-anhydroerythromycin A 6,9-hemiketal (Compound 25) as a white powder.

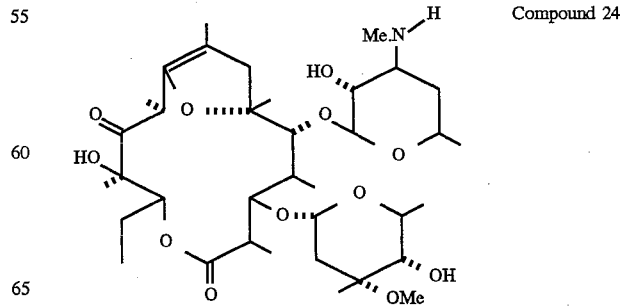

Compound 24

-continued

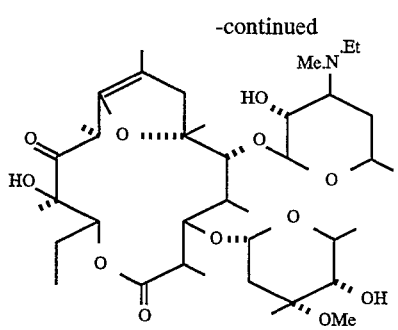

Compound 25

EXAMPLE 23

To a solution of Compound 24 (428 mg) in 7 ml of methanol were added 790 mg of di-isopropylethylamine and 4.16 g of isopropyl iodide, followed by stirring at 60° C. for 5 days. After the solvent was distilled off, the reaction solution was diluted with chloroform and washed with water and a saturated saline. The chloroform solution was dried over anhydrous sodium sulfate, and the solvent was distilled off. The resulting residue was purified by silica gel column chromatography [developing solvent: chloroform-methanol-conc. aqueous ammonia (100:1:0.1)] to yield 290 mg (yield: 64%) of isopropyl-nor-11-oxo-8,9-anhydroerythromycin A 6,9-hemiketal (Compound 26) as a white powder.

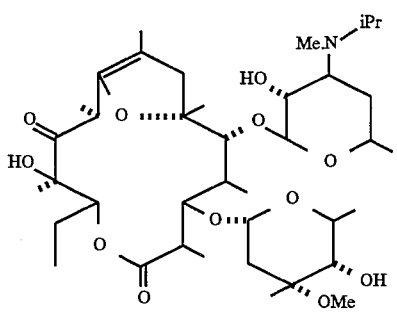

Compound 26

EXAMPLE 24

To a solution of Compound 23 (383 mg) in 4 ml of chloroform was added 0.34 ml of propargyl bromide, and the mixture was stirred at room temperature for 6 hours. After the solvent was distilled off, ether was added to the residue to provide a precipitate which was filtered off. The precipitate was washed with ether and then purified by silica gel column chromatography [developing solvent: chloroform-methanol-conc. aqueous ammonia (10:1:0.1)] to yield 251 mg (yield: 56%) of 11-oxo-8,9-anhydroerythromycin A 6,9-hemiketal propargyl bromide (Compound 27) as a white powder.

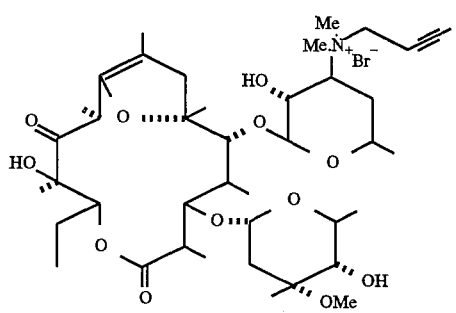

Compound 27

EXAMPLE 25

To a solution of Compound 4 (300 mg) in 5 ml of methanol were added 597 mg of di-isopropylethylamine and 456 mg of 3-chloro-1-butene, followed by stirring at 60° C. for 40 hours. After the solvent was distilled off, the reaction solution was diluted with chloroform and washed with water and a saturated saline. The chloroform solution was dried over anhydrous sodium sulfate, and the solvent was distilled off. The resulting residue was purified by silica gel column chromatography [developing solvent: chloroform-methanol-conc. aqueous ammonia (200:1:0.1)] to yield 81 mg (yield: 25%) of 2-(3-butenyl)-nor-12-O-methyl-11-oxo-8,9-anhydroerythromycin A 6,9-hemiketal (Compound 28) as a white powder.

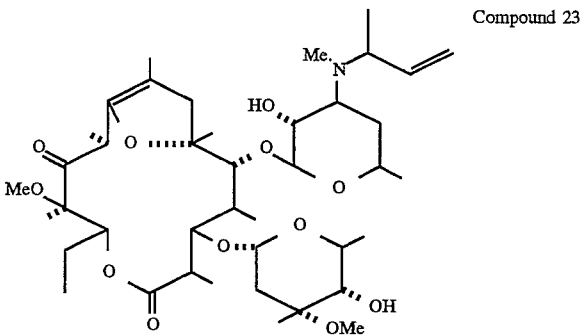

Compound 23

EXAMPLE 26

To a solution of Compound 4 (300 mg) in 5 ml of acetonitrile were added 543 mg of di-isopropylethylamine and 423 mg of 2-(1,3-difluoropropyl)trifluoromethanesulfonate, followed by stirring at 50° C. for 30 minutes. After the solvent was distilled off, the reaction solution was diluted with chloroform and washed with water and a saturated saline. The chloroform solution was dried over anhydrous sodium sulfate, and the solvent was distilled off. The resulting residue was purified by silica gel column chromatography [developing solvent: chloroform-methanol-conc. aqueous ammonia (250:1:0.1)] to yield 167 mg (yield: 50%) of 2-(1,3-difluoropropyl)-nor-12-O-methyl-11-oxo-8,9-anhydroerythromycin A 6,9-hemiketal (Compound 29) as a white powder.

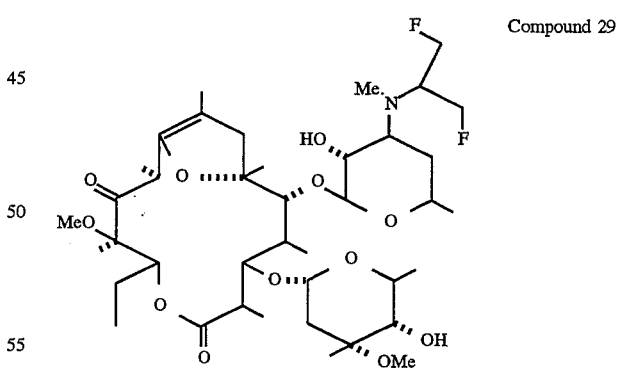

Compound 29

EXAMPLE 27

To a solution of Compound 4 (200 mg) in 5 ml of N,N-dimethylformamide were added 362 mg of di-isopropylethylamine, 1.0 g of 1-bromo-2-fluoroethane and 420 mg of sodium iodide, followed by stirring at 80° C. for 11 hours. The reaction solution was diluted with ethyl acetate, and washed with water and a saturated saline. The ethyl acetate solution was dried over anhydrous sodium sulfate, and the solvent was distilled off. The resulting residue was purified by silica gel column chromatography

[developing solvent: chloroform-methanol-conc. aqueous ammonia (250:1:0.1)] to yield 133 mg (yield: 63%) of 2-fluoroethyl-nor-12-O-methyl-11-oxo-8,9-anhydroerythromycin A 6,9-hemiketal (Compound 30) as a white powder.

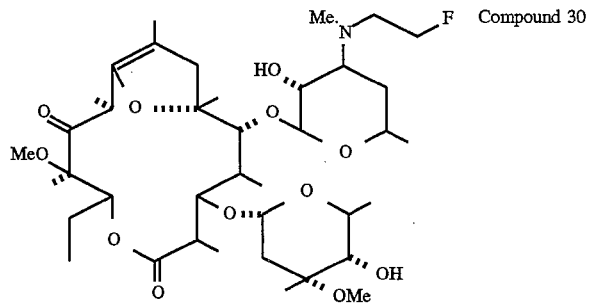

EXAMPLE 28

To a solution of Compound 4 (250 mg) in 4 ml of methanol were added 0.11 ml of cyclobutanone and 53 mg of sodium cyanoborohydride, followed by stirring at room temperature overnight. After the solvent was distilled off, the reaction solution was diluted with chloroform, and washed with water and a saturated saline. The chloroform solution was dried over anhydrous sodium sulfate, and the solvent was distilled off. The resulting residue was purified by silica gel column chromatography [developing solvent: chloroform-methanol-conc. aqueous ammonia (150:1:0.1)] to yield 192 mg (yield: 71%) of cyclobutyl-nor-12-O-methyl-11-oxo-8,9-anhydroerythromycin A 6,9-hemiketal (Compound 31) as a white powder.

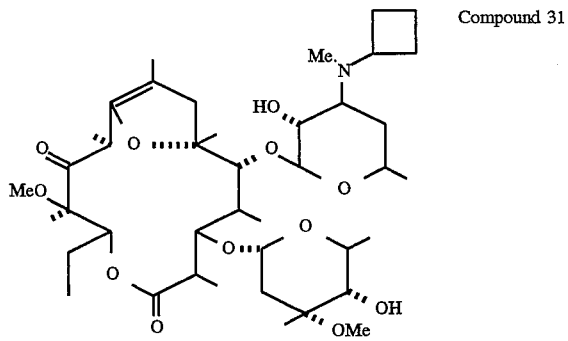

EXAMPLE 29

To a solution of Compound 4 (350 mg) in 6 ml of methanol were added 0.19 ml of cyclopentanone and 74 mg of sodium cyanoborohydride, followed by stirring at room temperature for 1 day. After the solvent was distilled off, the reaction solution was diluted with chloroform, and washed with water and a saturated saline. The chloroform solution was dried over anhydrous sodium sulfate, and the solvent was distilled off. The resulting residue was purified by silica gel column chromatography [developing solvent: chloroform-methanol-conc. aqueous ammonia (150:1:0.1)] to yield 250 mg (yield: 65%) of cyclopentyl-nor-12-O-methyl-11-oxo-8,9-anhydroerythromycin A 6,9-hemiketal (Compound 32) as a white powder.

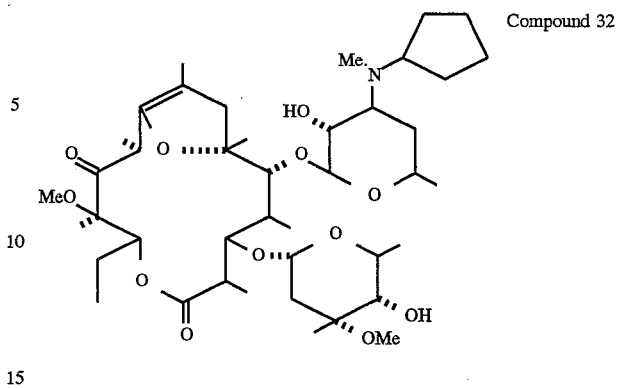

EXAMPLE 30

To a solution of Compound 4 (278 mg) in 6 ml of methanol were added 144 mg of tetrahydrofuran-3-one and 59 mg of sodium cyanoborohydride, followed by stirring at room temperature overnight. After the solvent was distilled off, the reaction solution was diluted with chloroform, and washed with water and a saturated saline. The chloroform solution was dried over anhydrous sodium sulfate, and the solvent was distilled off. The resulting residue was purified by silica gel column chromatography [developing solvent: chloroform-methanol-conc. aqueous ammonia (150:1:0.1)] to yield 177 mg (yield: 58%) of 3-tetrahydrofuranyl-nor-12-O-methyl-11-oxo-8,9-anhydroerythromycin A 6,9-hemiketal (Compound 33) as a white powder.

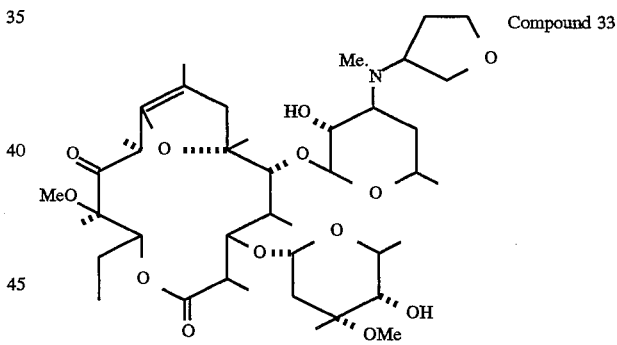

EXAMPLE 31

To a solution of Compound 4 (200 mg) in 5 ml of methanol were added 248 mg of tetrahydrothiophene-3-one and 84 mg of sodium cyanoborohydride, followed by stirring at room temperature for 2 days. After the solvent was distilled off, the reaction solution was diluted with chloroform, and washed with water and a saturated saline. The chloroform solution was dried over anhydrous sodium sulfate, and the solvent was distilled off. The resulting residue was purified by silica gel column chromatography [developing solvent: chloroform-methanol-conc. aqueous ammonia (230:1:0.1)] to yield 146 mg (yield: 65%) of 3-tetrahydrothiophenyl-nor-12-O-methyl-11-oxo-8,9-anhydroerythromycin A 6,9-hemiketal (Compound 84) as a white powder.

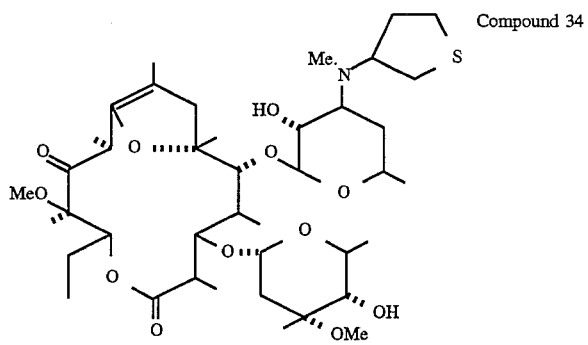

Compound 34

EXAMPLE 32

To a solution of Compound 4 (478 mg) in 10 ml of methanol were added 682 mg of 1-benzhydrylazetidine-3-one and 101 mg of sodium cyanoborohydride, followed by stirring at room temperature overnight. After the solvent was distilled off, the reaction solution was diluted with chloroform, and washed with water and a saturated saline. The chloroform solution was dried over anhydrous sodium sulfate, and the solvent was distilled off. The resulting residue was purified by silica gel column chromatography [developing solvent: chloroform-methanol-conc. aqueous ammonia (250:1:0.1)] to yield 667 mg (quantitative yield) of 3-(1-benzhydry-lazetidinyl)-nor-12-O-methyl-11-oxo-8,9-anhydroerythromycin A 8,9-hemiketal (Compound 35) as a white powder.

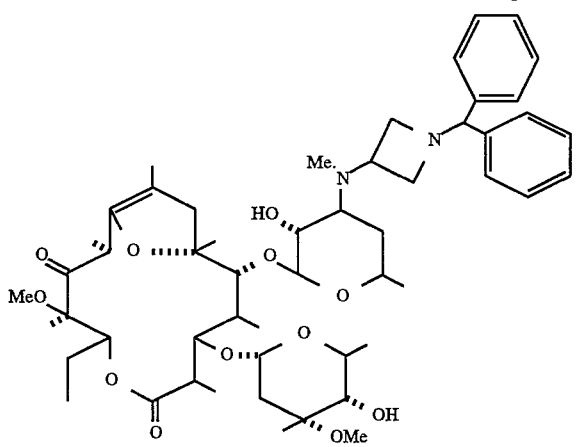

Compound 35

EXAMPLE 33

To a solution of Compound 35 (235 mg) in 6 ml of acetic acid was added 50 mg of Pearlman's catalyst, followed by stirring at room temperature overnight under hydrogen gas atmosphere. After the catalyst was removed by filtration, the reaction solution was diluted with dichloromethane, and washed with a saturated aqueous sodium bicarbonate and a saturated saline. The dichloromethane solution was dried over anhydrous sodium sulfate, and the solvent was distilled off. The resulting residue was purified by silica gel column chromatography [developing solvent: chloroform-methanol-conc. aqueous ammonia (10:1:0.1)] to yield 87 mg (yield: 41%) of 3-azetidinyl-nor-12-O-methyl-11-oxo-8,9-anhydroerythromycin A 6,9-hemiketal (Compound 36) as a white powder.

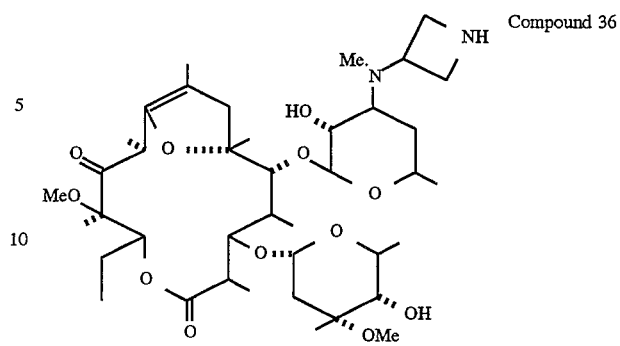

Compound 36

EXAMPLE 34

To a solution of Compound 4 (250 mg) in 5 ml of methanol were added 200 mg of 3-oxetanone and 53 mg of sodium cyanoborohydride, followed by stirring at room temperature for 2.5 hours. After the solvent was distilled off, the reaction solution was diluted with chloroform, and washed with water and a saturated saline. The chloroform solution was dried over anhydrous sodium sulfate, and the solvent was distilled off. The resulting residue was purified by silica gel column chromatography [developing solvent: chloroform-methanol-conc. aqueous ammonia (150:1:0.1)] to yield 120 mg (yield: 44%) of 3-oxetanyl-nor-12-O-methyl-11-oxo-8,9-anhydroerythromycin A 6,9-hemiketal (Compound 37) as a white powder.

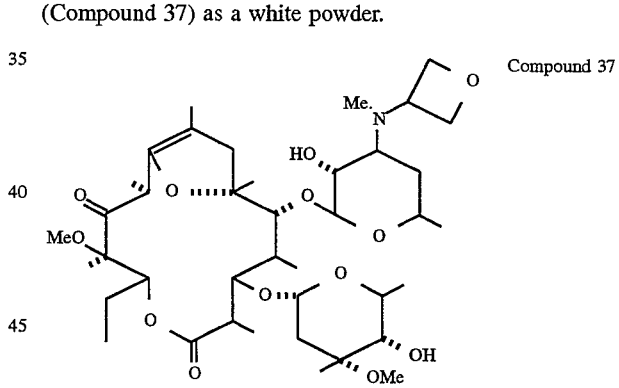

Compound 37

EXAMPLE 35

To a solution of Compound 4 (205 mg) in 5 ml of acetonitrile were added 297 mg of di-isopropylethylamine and 650 mg of 2,2,2-trifluoroethyl trifluoromethanesulfonate, followed by stirring at 50° C. overnight. After the solvent was distilled off, the reaction solution was diluted with chloroform and washed with water and a saturated saline. The chloroform solution was dried over anhydrous sodium sulfate, and the solvent was distilled off. The resulting residue was purified by silica gel column chromatography [developing solvent: chloroform-methanol-conc. aqueous ammonia (200:1:0.1)] to yield 132 mg (yield: 57%) of 2,2,2-trifluoroethyl-nor-12-O-methyl-11-oxo-8,9-anhydroerythromycin A 6,9-hemiketal (Compound 38) as a white powder.

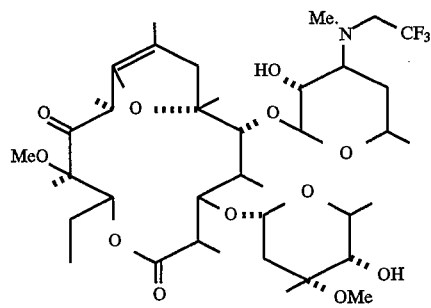

Compound 38

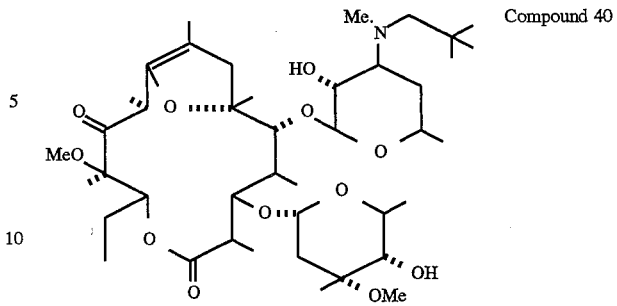

Compound 40

EXAMPLE 36

To a solution of Compound 4 (300 mg) in 7 ml of methanol were added 543 mg of di-isopropylethylamine and 3.09 g of 2-iodebutane, followed by stirring at 60° C. for 4 days. After the solvent was distilled off, the reaction solution was diluted with chloroform and washed with water and a saturated saline. The chloroform solution was dried over anhydrous sodium sulfate, and the solvent was distilled off. The resulting residue was purified by silica gel column chromatography [developing solvent: chloroform-methanol-conc. aqueous ammonia (150:1:0.1)] to yield 63 mg (yield: 20%) of 2-butyl-nor-12-O-methyl-11-oxo-8,9-anhydroerythromycin A 6,9-hemiketal (Compound 39) as a white powder.

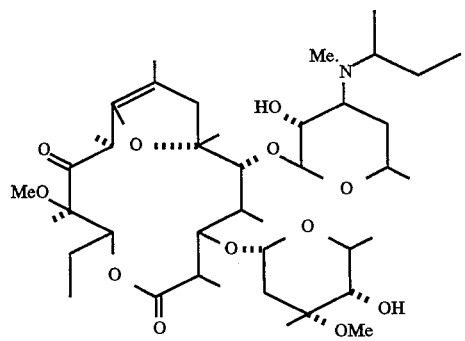

Compound 39

EXAMPLE 37

To a solution of Compound 4 (200 mg) in 4 ml of methanol were added 0.26 ml of pivalaldehyde and 84 mg of sodium cyanoborohydride, followed by stirring at room temperature for 40 hours. After the solvent was distilled off, the reaction solution was diluted with chloroform, and washed with water and a saturated saline. The chloroform solution was dried over anhydrous sodium sulfate, and the solvent was distilled off. The resulting residue was purified by silica gel column chromatography [developing solvent: chloroform-methanol-conc. aqueous ammonia (200:1:0.1)] to yield 128 mg (yield: 58%) of 2,2-dimethylpropyl-nor-12-O-methyl-11-oxo8,9-anhydroerythromycin A 6,9-hemiketal (Compound 40) as a white powder.

EXAMPLE 38

To a solution of Compound 4 (250 mg) in 6 ml of acetonitrile were added 452 mg of di-isopropylethylamine and 2.84 g of N-(2-bromoethyl)phthalimide, followed by stirring at 50° C. for 1 day. After the solvent was distilled off, the reaction solution was diluted with chloroform and washed with water and a saturated saline. The chloroform solution was dried over anhydrous sodium sulfate, and the solvent was distilled off. The resulting residue was purified by silica gel column chromatography [developing solvent: chloroform-methanol-conc. aqueous ammonia (100:1:0.1)] to yield 190 mg (yield: 61%) of 2-(N-phthalimidyl)ethyl-nor-12-O-methyl-11-oxo-8,9-anhydroerythromycin A 6,9-hemiketal (Compound 41) as a white powder.

To a solution of Compound 41 (190 mg) in 3 ml of methanol was added 1 ml of 40% methylamine-methanol solution, followed by stirring at room temperature for 2 hours. After the solvent was distilled off, the reaction solution was diluted with chloroform and washed with water and a saturated saline. The chloroform solution was dried over anhydrous sodium sulfate, and the solvent was distilled off. The resulting residue was purified by silica gel column chromatography [developing solvent: chloroform-methanol-conc. aqueous ammonia (15:1:0.1)] to yield 114 mg (yield: 70%) of 2-aminoethyl-nor-12-O-methyl-11-oxo-8,9-anhydroerythromycin A 6,9-hemiketal (Compound 42) as a white powder.

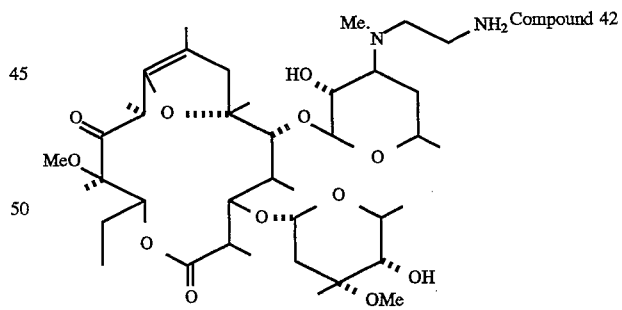

Compound 42

EXAMPLE 39

To a solution of Compound 4 (200 mg) in 5 ml of acetonitrile were added 362 mg of di-isopropylethylamine and 777 mg of α-chloroacetone, followed by stirring at room temperature overnight. After the solvent was distilled off, the reaction solution was diluted with chloroform and washed with water and a saturated saline. The chloroform solution was dried over anhydrous sodium sulfate, and the solvent was distilled off. The resulting residue was purified by silica gel column chromatography [developing solvent: chloroform-methanol-conc. aqueous ammonia (60:1:0.1)] to yield 196 mg (yield: 91%) of 2-oxopropyl-nor-12-O- methyl-11-oxo-8,9-anhydroerythromycin A 6,9-hemiketal (Compound 43) as a white powder.

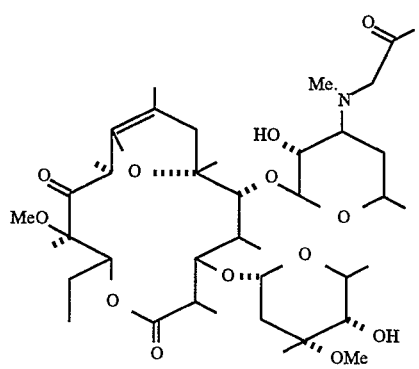

Compound 43

EXAMPLE 40

To a solution of Compound 43 (175 mg) in 3 ml of methanol was added 30 mg of sodium borohydride while cooling with ice, followed by stirring at room temperature for 7 hours. After the solvent was distilled off, the reaction solution was diluted with chloroform, and washed with water and a saturated saline. The chloroform solution was dried over anhydrous sodium sulfate, and the solvent was distilled off. The resulting residue was purified by silica gel column chromatography [developing solvent: chloroform-methanol-conc. aqueous ammonia (70:1:0.1)] to yield 132 mg (yield: 75%) of 2-hydroxypropyl-nor-12-O-methyl-11-oxo-8,9-anhydroerythromycin A 6,9-hemiketal (Compound 44) as a white powder.

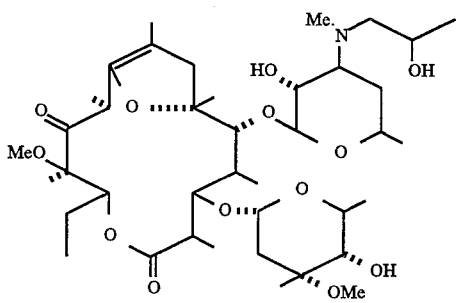

Compound 44

EXAMPLE 41

To a solution of Compound 4 (191 mg) in a mixture of 4 ml of acetonitrile and 4 ml of methanol were added 346 mg of di-isopropylethylamine and 750 mg of 2-chloroacetamide, followed by stirring at 50° C. overnight. After the solvent was distilled off, the reaction solution was diluted with chloroform and washed with water and a saturated saline. The chloroform solution was dried over anhydrous sodium sulfate, and the solvent was distilled off. The resulting residue was purified by silica gel column chromatography [developing solvent: chloroform-methanol-conc. aqueous ammonia (60:1:0.1)] to yield 141 mg (yield: 68%) of 2-acetamidyl-nor-12-O-methyl-11-oxo-8,9-anhydroerythromycin A 6,9-hemiketal (Compound 45) as a white powder.

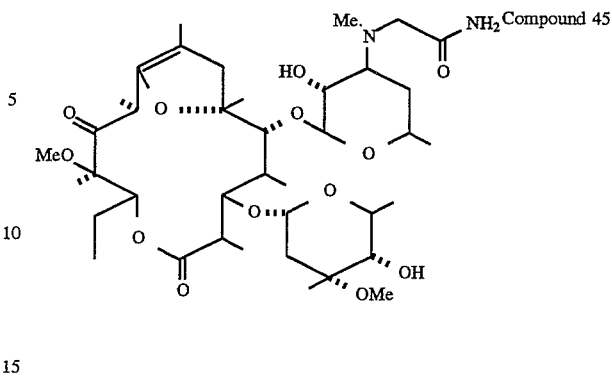

Compound 45

EXAMPLE 42

To a solution of Compound 4 (605 mg) in 6 ml of N,N-dimethylformamide were added 1.09 g of di-isopropylethylamine and 3.48 g of isobutyl bromide, followed by stirring at 50° C. for 1 day. After the solvent was distilled off, the reaction solution was diluted with chloroform, and washed with water and a saturated saline. The chloroform solution was dried over anhydrous sodium sulfate, and the solvent was distilled off. The resulting residue was purified by silica gel column chromatography [developing solvent: chloroform-methanol (300:1)] to yield 310 mg (yield: 47%) of isobutyl-nor-12-O-methyl-11-oxo-8,9-anhydroerythromycin A 6,9-hemiketal (Compound 46) as a white powder.

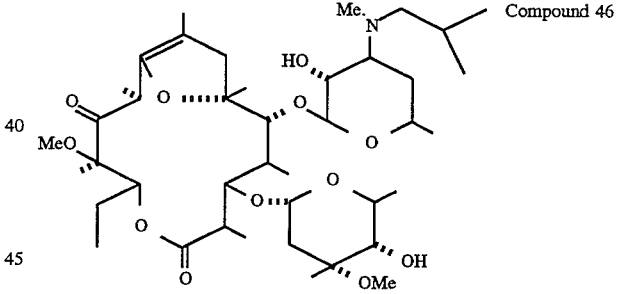

Compound 46

EXAMPLE 43

To a solution of Compound 13 (200 mg) in 7 ml of methanol were added 384 mg of α,α'-difluoroacetone and 180 mg of sodium cyanoborohydride, followed by stirring at room temperature for 1 day. After the solvent was distilled off, the reaction solution was diluted with chloroform, and washed with water and a saturated saline. The chloroform solution was dried over anhydrous sodium sulfate, and the solvent was distilled off. The resulting residue was purified by silica gel column chromatography [developing solvent: chloroform-methanol-conc. aqueous ammonia (250:1:0.1)] to yield 143 mg (yield: 64%) of 2-(1,3-difluoropropyl)-dinor-12-O-methyl-11-oxo-8,9-anhydroerythromycin A 6,9-hemiketal (Compound 47) as a white powder.

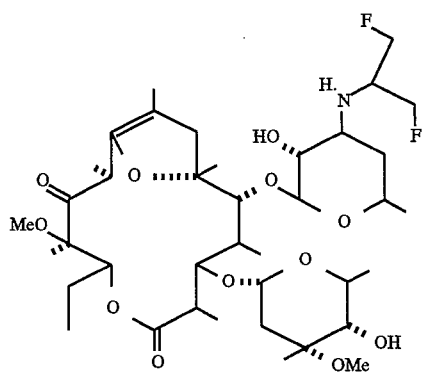

Compound 47

EXAMPLE 44

To a solution of Compound 13 (400 mg) in 10 ml of methanol were added 492 mg of 3-pentanone and 108 mg of sodium cyanoborohydride, followed by stirring at room temperature overnight. After the solvent was distilled off, the reaction solution was diluted with chloroform, and washed with water and a saturated saline. The chloroform solution was dried over anhydrous sodium sulfate, and the solvent was distilled off. The resulting residue was purified by silica gel column chromatography [developing solvent: chloroform-methanol-conc. aqueous ammonia (78:1:0.1)] to yield 194 mg (yield: 44%) of 8-pentyl-dinor-12-O-methyl-11-oxo-8,9-anhydroerythromycin A 6,9-hemiketal (Compound 48) as a white powder.

To a solution of Compound 48 (194 mg) in 6 ml of acetonitrile were added 216 mg of a formaldehyde solution, 40 mg of sodium cyanoborohydride and a drop of acetic acid, followed by stirring at room temperature for 1 hour. After the solvent was distilled off, the reaction solution was diluted with chloroform, and washed with water and a saturated saline. The chloroform solution was dried over anhydrous sodium sulfate, and the solvent was distilled off. The resulting residue was purified by silica gel column chromatography [developing solvent: chloroform-methanol-conc. aqueous ammonia (150:1:0.1)] to yield 154 mg (yield: 78%) of 3-pentyl-nor-12-O-methyl-11-oxo-8,9-anhydroerythromycin A 6,9-hemiketal (Compound 49) as a white powder.

Compound 49

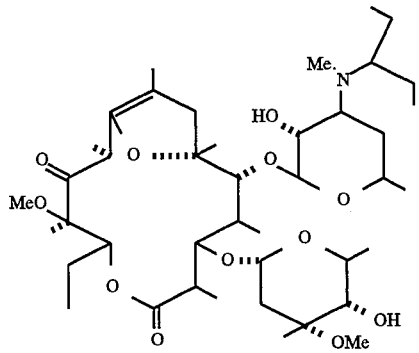

EXAMPLE 45

To a solution of Compound 13 (500 mg) in 5 ml of N,N-dimethylformamide were added 461 mg of di-isopropylethylamine and 2.4 g of 1,5-dibromopentane, followed by stirring at 50° C. overnight. After the solvent was distilled off, the reaction solution was diluted with chloroform, and washed with water and a saturated saline. The chloroform solution was dried over anhydrous sodium sulfate, and the solvent was distilled off. The resulting residue was purified by silica gel column chromatography [developing solvent: chloroform-methanol (300:1) to yield 184 mg (yield: 33%) of de(dimethylamino)-3'-piperidino-12-O-methyl-11-oxo-8,9-anhydroerythromycin A 6,9-hemiketal (Compound 50) as a white powder.

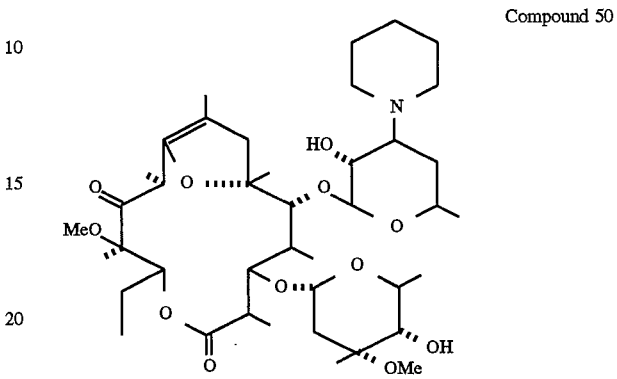

Compound 50

EXAMPLE 46

To a solution of Compound 13 (400 mg) in 5 ml of N,N-dimethylformamide were added 369 mg of di-isopropylethylamine and 1.85 g of 1,4-dibromobutane, followed by stirring at 50° C. overnight. After the solvent was distilled off, the reaction solution was diluted with chloroform, and washed with water and a saturated saline. The chloroform solution was dried over anhydrous sodium sulfate, and the solvent was distilled off. The resulting residue was purified by silica gel column chromatography [developing solvent: chloroform-methanol-conc. aqueous ammonia (60:1:0.1)] to yield 124 mg (yield: 29%) of de(dimethylamino)-3'-pyrrolidino-12-O-methyl-11-oxo-8,9-anhydroerythromycin A 8,9-hemiketal (Compound 51) as a white powder.

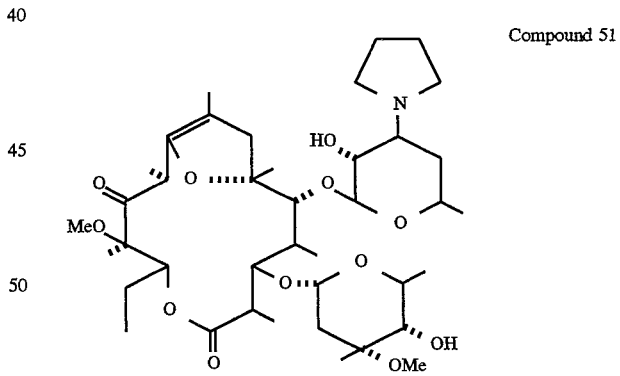

Compound 51

EXAMPLE 47

To a solution of Compound 22 (500 mg) in 10 ml of methanol were added 531 mg of ammonium acetate and 86 mg of sodium cyanoborohydride, followed by stirring at room temperature for 1 day. After the solvent was distilled off, the reaction solution was diluted with chloroform, and washed with water and a saturated saline. The chloroform solution was dried over anhydrous sodium sulfate, and the solvent was distilled off. The resulting residue was purified by silica gel column chromatography [developing solvent: chloroform-methanol-conc. aqueous ammonia (40:1:0.1)] to yield 123 mg (yield: 25%) of 4"-deoxy-4"-amino-12-O- methyl-11-oxo-8,9-anhydroerythromycin A 6,9-hemiketal (Compound 52) as a white powder.

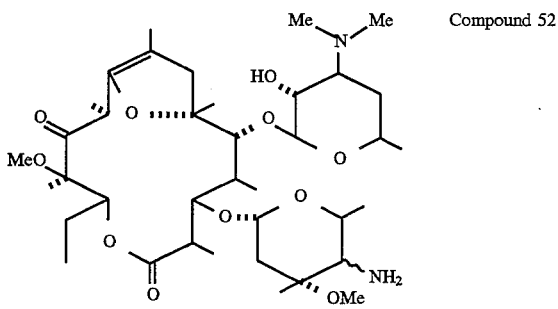

Compound 52

EXAMPLE 48

To a solution of Compound 22 (200 mg) in 10 ml of methanol was added 96 mg of hydroxylamine hydrochloride, followed by stirring at room temperature for 1 day. After the solvent was distilled off, the reaction solution was diluted with chloroform, and washed with water and a saturated saline. The chloroform solution was dried over anhydrous sodium sulfate, and the solvent was distilled off. The resulting residue was purified by silica gel column chromatography [developing solvent: chloroform-methanol-conc. aqueous ammonia (40:1:0.1)] to yield 109 mg (yield: 53%) of 4''-deoxy-4''-oximino-12-O-methyl-11-oxo-8,9-anhydroerythromycin A 6,9-hemiketal (Compound 53) as a white powder.

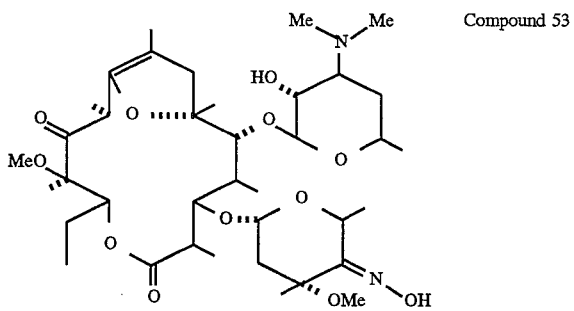

Compound 53

EXAMPLE 49

To a solution of Compound 24 (4.90 g) in 80 ml of 1,2-dichloroethane were added, while cooling with ice, 8.5 g of dimethylaminopyridine and 8.0 ml of benzyloxycarbonyl chloride, followed by stirring for 1 hour, and by an additional 19-hour stirring at room temperature. Water was added to the reaction solution which was then extracted with dichloromethane, and washed with a saturated saline. The dichloromethane solution was dried over anhydrous sodium sulfate, and the solvent was distilled off. The resulting residue was purified by silica gel column chromatography [developing solvent: chloroform-methanol (70:1)] to yield 1.38 g (yield: 18%) of N-demethyl-2'-O,4''-O,3'-N-tris(benzyloxycarbonyl)-11-oxo-8,9-anhydroery-thromycin A 8,9-hemiketal (Compound 54) as a white powder.

To a solution of Compound 54 (600 mg) in 10 ml of N,N-dimethylformamide was added, while cooling with ice, 33 mg of sodium hydride. The mixture was stirred for 15 minutes, and 0.085 ml of ethyl iodide was added thereto, followed by stirring for 1 hour. A saturated aqueous sodium bicarbonate was added to the reaction solution which was then extracted with ethyl acetate. The ethyl acetate solution was washed with water and a saturated saline, and then dried over anhydrous sodium sulfate, and the solvent was distilled off. The resulting residue was purified by silica gel column chromatography [developing solvent: chloroform-methanol (100:1)] to yield 305 mg (yield: 53%) of N-demethyl-2'-O, 4''-O,3'-N-tris(benzyloxycarbonyl)-12-O-ethyl-11-oxo-8,9-anhydroerythromycin A 6,9-hemiketal (Compound 55) as a white powder.

To a solution of Compound 55 (300 mg) in 8 ml of ethanol was added 50 mg of 10% Pd on carbon, and the mixture was stirred at room temperature overnight under hydrogen gas atmosphere. Thereafter 228 mg of a formaldehyde solution was added to the mixture which was then stirred for 6 hours under hydrogen gas atmosphere. The reaction solution was filtered, and the solvent was distilled off. The resulting residue was purified by silica gel column chromatography [developing solvent: chloroform-methanol-conc. aqueous ammonia (40:1:0.1)] to yield 146 mg (yield: 74%) of 12-O-ethyl-11-oxo-8,9-anhydroerythromycin A 6,9-hemiketal (Compound 56) as a white powder.

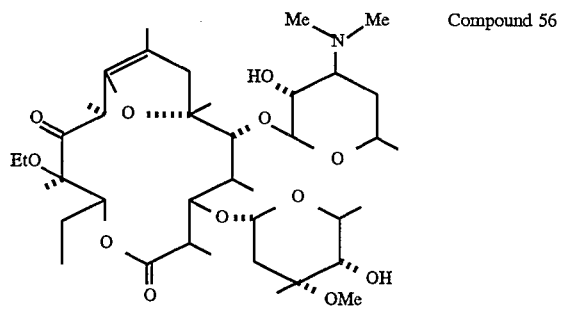

Compound 56

EXAMPLE 50

To a solution of Compound 54 (219 mg) in 3 ml of N,N-dimethylformamide was added, while cooling with ice, 12 mg of sodium hydride. The mixture was stirred for 15 minutes, and 0.047 ml of benzyl bromide was added thereto, followed by stirring for 1 hour. A saturated aqueous sodium bicarbonate was added to the reaction solution which was then extracted with ethyl acetate. The ethyl acetate solution was washed with water and a saturated saline, and then dried over anhydrous sodium sulfate, and the solvent was distilled off. The resulting residue was purified by silica gel column chromatography [developing solvent: ethyl acetate-n-hexane (1:2)] to yield 179 mg (yield: 75%) of N-demethyl-2'-O, 4''-O,3'-N-tris(benzyloxycarbonyl)-12-O-benzyl-11-oxo-8,9-anhydroerythromycin A 6,9-hemiketal (Compound 57) as a white powder.

To a solution of Compound 57 (175 mg) in 4 ml of ethanol was added 27 mg of 10% Pd on carbon, and the mixture was stirred at room temperature overnight under hydrogen gas atmosphere. Thereafter 71 mg of a formaldehyde solution was added to the mixture which was then stirred for 8 hours under hydrogen gas atmosphere. The reaction solution was filtered, and the solvent was distilled off. The resulting residue was purified by silica gel column chromatography [developing solvent: chloroform-methanol-conc. aqueous ammonia (70:1:0.1)] to yield 121 mg (quantitative yield) of 12-O-benzyl-11-oxo-8,9-anhydroerythromycin A 6,9-hemiketal (Compound 58) as a white powder.

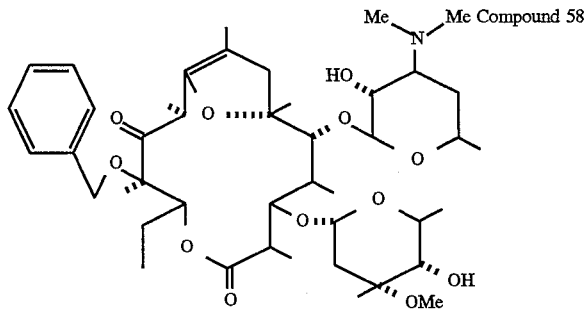

Compound 58

EXAMPLE 51

To a solution of Compound 54 (264 mg) in 3 ml of N,N-dimethylformamide was added, while cooling with ice, 19 mg of sodium hydride. The mixture was stirred for 15 minutes, and 0.070 ml of n-propyl iodide was added thereto, followed by stirring for 2 hour. A saturated aqueous sodium bicarbonate was added to the reaction solution which was then extracted with ethyl acetate. The ethyl acetate solution was washed with water and a saturated saline, and then dried over anhydrous sodium sulfate, and the solvent was distilled off. The resulting residue was purified by silica gel column chromatography [developing solvent: ethyl acetate-n-hexane (1:2)] to yield 133 mg (yield: 48%) of N-demethyl-2'-O, 4"-O,3'-N-tris(benzyloxycarbonyl)-12-O-propyl-11-oxo-8,9-anhydroerythromycin A 6,9-hemiketal (Compound 59) as a white powder.

To a solution of Compound 59 (133 mg) in 4 ml of ethanol was added 20 mg of 10% Pd on carbon, and the mixture was stirred at room temperature overnight under H₂ gas atmosphere. Thereafter 96 mg of a formaldehyde solution was added to the mixture which was then stirred for 5 hours under H₂ gas atmosphere. The reaction solution was filtered, and the solvent was distilled off. The resulting residue was purified by silica gel column chromatography [developing solvent: chloroform-methanol-conc. aqueous ammonia (70:1:0.1)] to yield 80 mg (yield: 91%) of 12-O-propyl-11-oxo-8,9- anhydroerythromycin A 6,9-hemiketal (Compound 60) as a white powder.

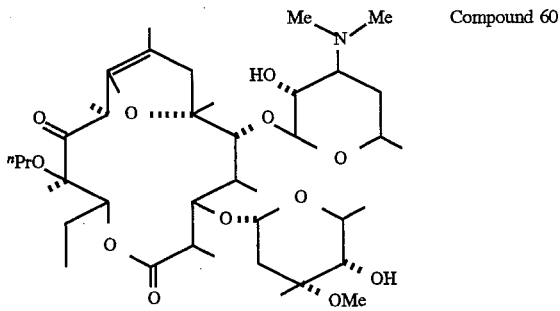

Compound 60

EXAMPLE 52

To a solution of Compound 6 (10.5 g) in 70 ml of dichloromethane were added 4.5 ml of pyridine and then 2.6 ml of acetic anhydride, followed by stirring at room temperature for 2 hours. To the reaction solution was added a saturated aqueous sodium bicarbonate, followed by extraction with dichloromethane. The dichloromethane solution was dried over anhydrous sodium sulfate, and thereafter the solvent was distilled off. The resulting residue was purified by silica gel column chromatography [developing solvent: chloroform-methanol (250:1)] to yield 8.5 g (yield: 76%) of isopropyl-nor-2'-O-acetyl-12-O-methyl-11-oxo-8,9-anhydroerythromycin A 6,9-hemiketal (Compound 61) as a white powder.

EXAMPLE 53

To a solution of Compound 61 (8.5 g) in 70 ml of dichloromethane were added 5.20 g of dimethylaminopyridine and 6.33 g of 1,1'-thiocarbonyldiimidazole, followed by stirring at room temperature for 3 days. A 3 ml portion of a conc. aqueous ammonia was added to the reaction solution which was then stirred for 15 minutes. Thereafter dichloromethane was added to the solution which was then washed with a saturated aqueous sodium bicarbonate. The organic layer was dried over anhydrous sodium sulfate and the solvent was distilled off. The resulting residue was purified by silica gel column chromatography [developing solvent: chloroform-methanol (400:1)] to give 7.50 g (yield: 77%) of isopropyl-nor-2'-O-acetyl-4"-O-thiocarbonylimidazolyl-12-O-methyl-11-oxo-8,9-anhydroerythromycin A 8,9-hemiketal (Compound 62) as a white powder.

A solution of Compound 62 (350 mg), 243 mg of triphenyltin hydride and 13 mg of α,α'-azobis (isobutyronitrile) in 7 ml of toluene was heated to reflux for 2 hours. A saturated aqueous sodium bicarbonate was added to the reaction solution which was then extracted with ethyl acetate. The ethyl acetate solution was dried over anhydrous sodium sulfate, and the solvent was distilled off. The resulting residue was purified by silica gel column chromatography [developing solvent: ethyl acetate-n-hexane (1:2)] to yield 156 mg (yield: 52%) of isopropyl-nor-2'-O-acetyl-4"-deoxy-12-O-methyl-11-oxo-8,9-anhydroerythromycin A 6,9-hemiketal (Compound 63) as a white powder.

To Compound 63 (153 mg) were added 3 ml of methanol and 0.5 ml of dichloromethane for dissolution, and 0.3 ml of a saturated aqueous sodium bicarbonate was added to the solution which was then stirred at room temperature overnight. Water was added to the reaction solution which was then extracted with dichloromethane. The dichloromethane solution was dried over anhydrous sodium sulfate, and the solvent was distilled off. The resulting residue was then purified by silica gel column chromatography [developing solvent: chloroform-methanol-conc. aqueous ammonia (100:1:0.1)] to yield 129 mg (yield: 89%) of isopropyl-nor-4"-deoxy-12-O-methyl-11-oxo-8,9-anhydroerythromycin A 6,9-hemiketal (Compound 64) as a white powder.

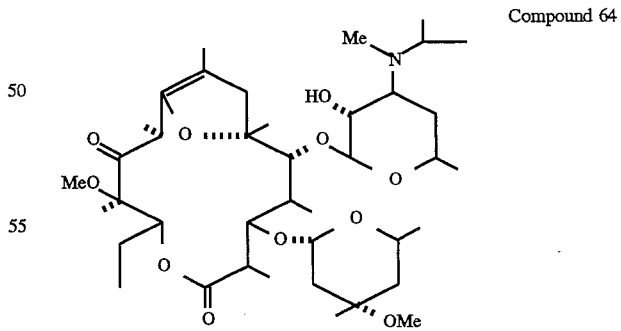

Compound 64

EXAMPLE 54

A solution of Compound 64 (3.60 g) and 2.0 g of sodium acetate in 70 ml of 80% methanol/water was heated to 55° C., and, while stirring, 1.85 mg of iodine was added to the solution. The mixture was stirred at that temperature for 1 hour while keeping its pH at 8–9 by addition of an appropriate amount of 1N aqueous solution of sodium hydroxide.

The reaction solution was poured into 50 ml of water which contained 3 ml of conc. aqueous ammonia, extracted with chloroform, dried over anhydrous sodium sulfate, and thereafter the solvent was distilled off. The resulting residue was purified by silica gel column chromatography [developing solvent: chloroform-methanol-conc. aqueous ammonia (15:1:0.1)] to yield 712 mg (yield:21%) of de(N-methyl)-4"-deoxy-12-O-methyl-11-oxo-8,9-anhydroerythromycin A 6,9-hemiketal (Compound 65) as a white powder.

To a solution of Compound 65 (430 mg) in 10 ml of ethanol were added 528 mg of a formaldehyde solution, 0.070 ml of acetic acid and 90 mg of 10% Pd on carbon, and the mixture was stirred at room temperature for 1 day under hydrogen gas atmosphere. The reaction solution was filtered, the solvent was distilled off, and a saturated aqueous sodium bicarbonate was added to the resulting residue, followed by extraction with dichloromethane. The dichloromethane solution was dried over anhydrous sodium sulfate, and the solvent was distilled off. The resulting residue was purified by silica gel column chromatography [developing solvent: chloroform-methanol-conc. aqueous ammonia (100:1:0.1)] to yield 327 mg (yield: 74%) of 4"-deoxy-12-O-methyl-11-oxo-8,9-anhydroerythromycin A 6,9-hemiketal (Compound 66) as a white powder.

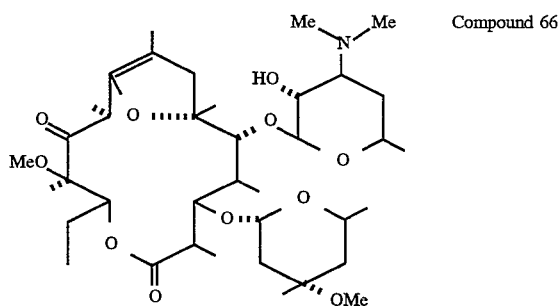

EXAMPLE 55

To a solution of Compound 65 (278 mg) in 5 ml of methanol were added 0.56 ml of di-isopropylethylamine and 0.19 ml of ethyl iodide, followed by stirring at room temperature for 5 days. After the solvent was distilled off, the reaction solution was diluted with chloroform and washed with water and a saturated saline. The chloroform solution was dried over anhydrous sodium sulfate, and the solvent was distilled off. The resulting residue was purified by silica gel column chromatography [developing solvent: chloroform-methanol-conc. aqueous ammonia (100:1:0.1)] to yield 149 mg (yield: 51%) of ethyl-nor-4"-deoxy-12-O-methyl-11-oxo-8,9-anhydroerythromycin A 6,9-hemiketal (Compound 67) as a white powder.

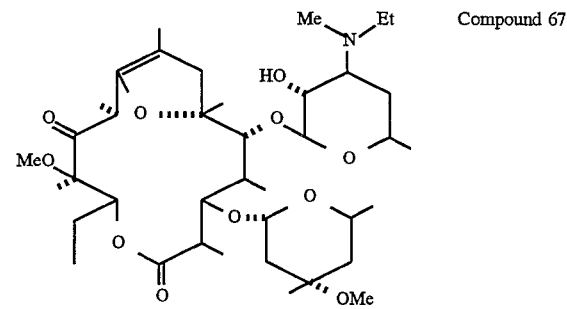

EXAMPLE 56

To a solution of Compound 65 (591 mg) in 10 ml of methanol were added 1.09 g of di-isopropylethylamine and 6.23 g of 2-iodebutane, followed by stirring at 50° C. for 4 days. After the solvent was distilled off, the reaction solution was diluted with chloroform and washed with water and a saturated saline. The chloroform solution was dried over anhydrous sodium sulfate, and the solvent was distilled off. The resulting residue was purified by silica gel column chromatography [developing solvent: chloroform-methanol (400:1)] to yield 261 mg (yield: 40%) of 2-butyl-nor-4"-deoxy-12-O-methyl-11-oxo-8,9-anhydroerythromycin A 6,9-hemiketal (Compound 68) as a white powder.

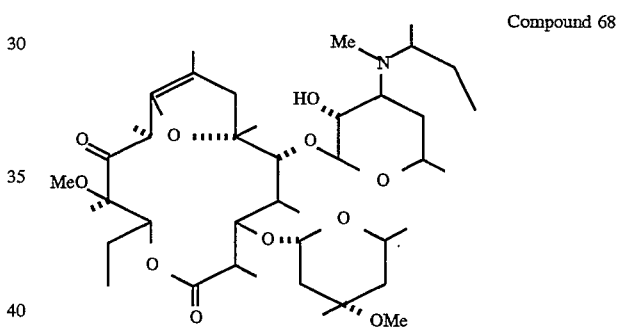

EXAMPLE 57

Compound 6 (187 mg) and fumaric acid (28.5 mg) were dissolved in 0.3 ml of hot methanol to give a solution. Isopropyl alcohol (1.0 ml) was added to the solution and the resulting mixture was left at room temperature to allow crystals to separate out. The crystals were collected by filtration to yield isopropyl-nor-12-O-methyl-11-oxo-8,9-anhydroerythromycin A 6,9-hemiketal fumarate monohydrate (Compound 69) as a colorless belonite. m.p. 135°–137° C.

Element analysis for $C_{42}H_{73}NO_{15}$: Calculated (%): C 60.63, H 8.84, N 1.68 Found (%): C 60.67, H 8.78, N 1.71

Compound 69

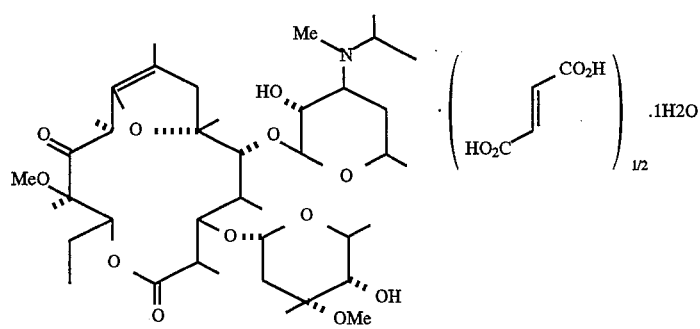

EXAMPLE 58

Compound 6 (100 mg) and succinic acid (15.6 mg) were dissolved in 0.3 ml of hot methanol to give a solution. Isopropyl alcohol (1.0 ml) was added to the solution and the resulting mixture was left at room temperature to allow crystals to separate out. The crystals were collected by filtration to yield isopropyl-nor-O-methyl-11-oxo-8,9-anhydroerythromycin A 6,9-hemiketal succinate (Compound 70) as a colorless belonite. m.p. 115°–121° C.

Tables 1-1 and 1-2 summarize the various physical values of Compounds 2–70 which were obtained in Examples 1–58 described above, but excluding Compounds 24, 41, 48, 54, 55, 57, 59, 61–63 and 65.

Compound 70

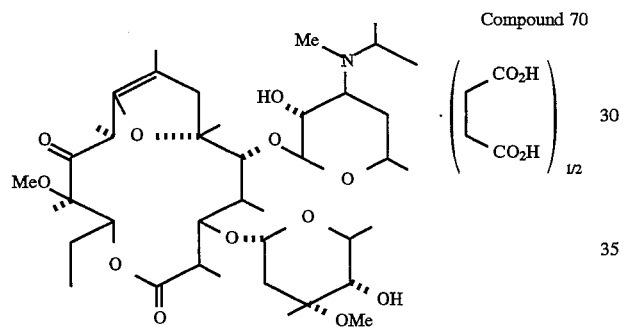

TABLE 1-1

| Compound No. | $[\alpha]_D^{25}$ (c1.0) (solvent) | $^1$H-NMR (δ value) | | | | FAB-MS |
| | | 8-Me | 3'-NMe | 3"-OMe | 12-OMe | solvent | (m/z) |
|---|---|---|---|---|---|---|---|
| 2  | +14.6° (CHCl₃) | 1.65 | 2.24 | 3.33 | —    | CDCl₃ | 785(MH⁺) |
| 3  | +48.6° (CHCl₃) | 1.68 | 2.28 | 3.35 | 3.06 | CDCl₃ | 728(M⁺) |
| 4  | +40.0° (CHCl₃) | 1.68 | 2.41 | 3.34 | 3.06 | CDCl₃ | 715(MH⁺) |
| 5  | +50.4° (CHCl₃) | 1.68 | 2.23 | 3.34 | 3.06 | CDCl₃ | 743(MH⁺) |
| 6  | +47.4° (CHCl₃) | 1.68 | 2.20 | 3.35 | 3.06 | CDCl₃ | 757(MH⁺) |
| 7  | +53.8° (CHCl₃) | 1.68 | 2.22 | 3.34 | 3.05 | CDCl₃ | 757(MH⁺) |
| 8  | +48.8° (CHCl₃) | 1.68 | 2.22 | 3.32 | 3.06 | CDCl₃ | 755(MH⁺) |
| 9  | +51.6° (CHCl₃) | 1.68 | 2.34 | 3.33 | 3.06 | CDCl₃ | 753(MH⁺) |
| 10 | +47.4° (CHCl₃) | 1.67 | 2.25 | 3.34 | 3.05 | CDCl₃ | 769(MH⁺) |
| 11 | +46.4° (CHCl₃) | 1.68 | 2.34 | 3.33 | 3.06 | CDCl₃ | 759(MH⁺) |
| 12 | +52.0° (CHCl₃) | 1.68 | 2.33 | 3.34 | 3.05 | CDCl₃ | 769(MH⁺+1) |
| 13 | +37.6° (CHCl₃) | 1.68 | —    | 3.32 | 3.06 | CDCl₃ | 701(MH⁺) |
| 14 | +60.4° (CHCl₃) | 1.67 | —    | 3.34 | 3.06 | CDCl₃ | 757(MH⁺) |
| 15 | +52.6° (CHCl₃) | 1.68 | —    | 3.33 | 3.05 | CDCl₃ | 729(MH⁺) |
| 16 | +37.2° (CHCl₃) | 1.67 | —    | 3.30 | 3.05 | CDCl₃ | 781(MH⁺) |
| 17 | +49.2° (CHCl₃) | 1.68 | —    | 3.32 | 3.05 | CDCl₃ | 741(MH⁺) |
| 18 | +52.4° (CHCl₃) | 1.68 | —    | 3.34 | 3.06 | CDCl₃ | 743(MH⁺) |
| 19 | +37.8° (MeOH)  | 1.71 | 3.27 | 3.36 | 3.07 | CD₃OD | 743(M⁺-I) |
| 20 | +31.0° (MeOH)  | 1.71 | 3.26 | 3.37 | 3.06 | CD₃OD | 767(M⁺-Br) |
| 21 | +35.8° (CHCl₃) | 1.66 | 2.24 | 3.33 | 3.06 | CDCl₃ | 769(MH⁺) |
| 22 | +42.2° (CHCl₃) | 1.68 | 2.26 | 3.32 | 3.07 | CDCl₃ | 727(MH⁺) |
| 23 | +25.0° (CHCl₃) | 1.66 | 2.27 | 3.31 | —    | CDCl₃ | 714(M⁺) |
| 25 | +27.5° (CHCl₃) | 1.66 | 2.22 | 3.31 | —    | CDCl₃ | 729(MH⁺) |
| 26 | +25.2° (CHCl₃) | 1.66 | 2.21 | 3.32 | —    | CDCl₃ | 742(M⁺) |
| 27 | +28.0° (MeOH)  | 1.53 | 3.07 | 3.18 | —    | CD₃OD | 753(M⁺-Br) |

TABLE 1-2

| Compound No. | $[\alpha]_D^{25}$ (c1.0, CHCl$_3$) | FAB-MS (m/z) | 1H-NMR (δ value) CDCl$_3$ 8-Me | 3'-NMe | 3"-OMe | 12-OMe | Other value |
|---|---|---|---|---|---|---|---|
| 28 | +51.6° | 769(MH$^+$) | 1.67 | 2.19 | 3.32 | 3.06 | |
| 29 | +49.6° | 793(MH$^+$) | 1.68 | 2.41 | 3.33 | 3.05 | |
| 30 | +52.2° | 762(MH$_2^+$) | 1.68 | 2.34 | 3.33 | 3.05 | |
| 31 | +46.6° | 769(MH$^+$) | 1.68 | 2.05 | 3.32 | 3.05 | |
| 32 | +45.2° | 784(MH$_2^+$) | 1.67 | 2.17 | 3.34 | 3.05 | |
| 33 | +41.6° | 786(MH$_2^+$) | 1.68 | 2.24(1.5H) 2.19(1.5H) | 3.33 | 3.05 | |
| 34 | +47.2° | 802(MH$_2^+$) | 1.68 | 2.27 | 3.33 | 3.05 | |
| 35 | +32.4° | 936(MH$^+$) | 1.67 | 2.06 | 3.21 | 3.05 | 7.16–7.41(m, 10H) |
| 36 | +45.8° | 770(MH$^+$) | 1.68 | 2.12 | 3.31 | 3.06 | |
| 37 | +50.8° | 771(MH$^+$) | 1.68 | 2.23 | 3.31 | 3.05 | |
| 38 | +41.2° | 797(MH$^+$) | 1.68 | 2.46 | 3.33 | 3.06 | |
| 39 | +48.2° | 772(MH$_2^+$) | 1.68 | 2.25(1.5H) 2.13(1.5H) | 3.35 | 3.06 | |
| 40 | +48.4° | 784(M$^+$) | 1.68 | 2.27 | 3.32 | 3.06 | |
| 42 | +56.0° | 758(MH$^+$) | 1.68 | 2.28 | 3.34 | 3.06 | |
| 43 | +39.0° | 771(MH$^+$) | 1.67 | 2.21 | 3.35 | 3.05 | 2.00(s, 3H) |
| 44 | +56.2° | 773(MH$^+$) | 1.68 | 2.40(1.5H) 2.32(1.5H) | 3.33 | 3.05 | |
| 45 | +52.2° | 772(MH$^+$) | 1.69 | 2.39 | 3.31 | 3.06 | |
| 46 | +51.6° | 770(M$^+$) | 1.68 | 2.21 | 3.34 | 3.06 | 2.92(d, 2H, J=15Hz) |
| 47 | +54.0° | 779(MH$^+$) | 1.68 | — | 3.33 | 3.06 | |
| 49 | +52.6° | 785(MH$^+$) | 1.67 | 2.17 | 3.35 | 3.06 | |
| 50 | +53.4° | 769(MH$^+$) | 1.67 | — | 3.33 | 3.05 | |
| 51 | +48.8° | 755(MH$^+$) | 1.68 | — | 3.34 | 3.06 | |
| 52 | +43.6° | 727(M$^+$) | 1.68 | 2.27 | 3.33(1.5H) 3.32(1.5H) | 3.06 | |
| 53 | +62.2° | 741(M$^+$) | 1.68 | 2.26 | 3.30 | 3.07 | |
| 56 | +47.2° | 742(M$^+$) | 1.68 | 2.28 | 3.34 | — | |
| 58 | +40.6° | 805(MH$^+$) | 1.68 | 2.28 | 3.35 | — | |
| 60 | +47.8° | 756(M$^+$) | 1.68 | 2.28 | 3.34 | — | |
| 64 | +65.0° | 740(M$^+$) | 1.67 | 2.20 | 3.27 | 3.06 | |
| 66 | +62.4° | 713(MH$^+$) | 1.67 | 2.27 | 3.26 | 3.06 | |
| 67 | +66.0° | 727(MH$^+$) | 1.67 | 2.22 | 3.26 | 3.06 | |
| 68 | +60.4° | 755(MH$^+$) | 1.67 | 2.23(1.5H) 2.12(1.5H) | 3.27 | 3.06 | |
| 69 | — | — | 1.71 | 2.69 | 3.35 | 3.07 | 6.67(s, 1H) |
| 70 | — | — | 1.71 | 2.57 | 3.35 | 3.06 | 2.51 |

(a) As regards Compounds 69 and 70, CD$_3$OD was used instead of CDCl$_3$.

TEST EXAMPLE 1

A motilin receptor binding test was conducted in the manner described hereunder [V. Bormans, et al., Regul. Peptides, 15, 143 (1986)].

From a killed rabbit was removed the duodenum, of which the mucous membrane was detached from the tunica muscularis and then homogenized in a 50 mM Tris solution (pH 7.4) to prepare a protein solution. Twenty-five pM of $^{125}$I-labelled motilin (purchased from Ohtsuka Assay Laboratory) and the protein solution were incubated at 25° C. for 120 minutes, after which the radioactivity of the protein was measured with a γ-ray counter, the difference between the radioactivity observed in the case of non-addition of motilin and that observed in the case of addition of an excess (1×10$^{-7}$ m) of motilin being defined as the specific binding capacity. The efficacies of the samples were expressed as IC$_{50}$ (M), the concentration of each of the test drugs which reduces the specific binding capacity to 50%. The test drug was dissolved in a DMSO solution and added to the protein solution (the final DMSO concentration:1%). In experiments on investigation of the acid resistance, the test drug was dissolved in a hydrochloric acid solution (pH 2.5) which was then allowed to stand at room temperature for 120 minutes prior to its addition to the protein solution for the experiments.

As a result, the IC$_{50}$ (M) in the DMSO solution was 4.1×10$^{-9}$ for Compound 6, whereas the value was 2.6×10$^{-9}$ for EM-523, and thus these two test drugs were found to have the same level of activity. In the hydrochloric acid solution, the IC$_{50}$ (M) of EM-523 was 2.6×10$^{-7}$, a decrease in the activity to one-100th that in the DMSO solution, while the IC50 (M) of Compound 6 was 9.1×10$^{-9}$, differing little from the value in the DMSO solution. The foregoing facts have proved that Compound 6 is less decomposable with an acid than is EM-523.

TABLE 2

| | IC$_{50}$ (M) | |
|---|---|---|
| | Solution in DMSO | Solution in HCl |
| EM-523 | 2.6 × 10$^{-9}$ | 2.6 × 10$^{-7}$ |
| Compound 6 | 4.1 × 10$^{-9}$ | 9.1 × 10$^{-9}$ |

TEST EXAMPLE 2

The gastrointestinal motility of the conscious dog was measured according to the method described previously [Itoh, Zen, Journal of the Smooth Muscle Research, 13, 33 (1976)]. Beagle dogs weighing approximately 10 kg were anesthetized with an intravenously (i.v.) injection of pentobarbital sodium and the abdominal cavity was opened under aseptic conditions. Extraluminal force transducers were sutured onto the serosa of the gastric antrum (stomach), duodenum and jejunum in a manner to measure circular muscle contraction. In addition, a Silastic tube [French, size 6.5, Dow Corning, Midland, Mich., U.S.A.) was placed into the stomach for direct administration of test drugs into the stomach. The lead wires of these force transducers and a Silastic tube were led out of the abdominal cavity and through a skin incision made between the scapulae. After the operation, the dogs were housed in individual experimental cages and given commercial dog food once a day.

The gastrointestinal motor activity was recorded on a thermal pen-writing recorder (WR-3101, Graphtec, Tokyo, Japan) by connecting the lead wires of the transducers to the connecting cables from the amplifiers (UG-5, Nihon Kohden, Tokyo, Japan). About 2 weeks postoperatively, gastrointestinal contractile activity could be divided into two main patterns of activity, interdigestive and digestive state. In the interdigestive state, IMC (interdigestive migrating contractions) were seen to occur at regular intervals of 100–120 minutes in the gastric antrum and migrated through the duodenum and jejunum at a constant velocity. In all animals, feeding disrupted the regular IMC pattern. Experiments were carried out during interdigestive state. The test drug was directly injected into the stomach through a Silastic tube placed in the stomach in a volume of 3 ml, 15 min after the end of the IMC in the gastric antrum. Test drugs were dissolved in ethanol, and then diluted with 0.9% physiological saline.

To measure motility quantitatively, the signals from the gastric antrum were relayed to a personal computer (PC-9801, NEC, Tokyo, Japan) every 100 ms. The area surrounded by the contraction waves and the base line, i.e., the product of the amplitude (voltage) and the time in minutes during a certain fixed period, was calculated, expressed as percent of the area assuming that maximum contraction (amplitude) of the interdigestive migrating contraction lasted for 1 min, and used as the motor index (MI) [Inatomi et al., J. Pharmacol. Exp. Ther. 251, 707 (1989)]. The MI, which is calculated in this manner, of the naturally occurred in the gastric antrum is about 100–200. Therefore, the test drug dosage required to provide MI=150 was defined to be $MI_{150}$ which was used as the index of the stimulating effects or the gastric motility of test drugs.

EM-523 and Compound 6 administered into the stomach increased gastrointestinal contractile activity, and the $MI_{150}$ values were 14.6 μg/kg and 3.8 μg/kg, respectively. Compound 6 showed about 4 times more potent contractile activity in the gastric antrum than EM-523.

INDUSTRIAL APPLICABILITY

The erythromycin derivatives of the present invention which have an enterokinesis stimulating action are characterized in that they undergo a remarkably lower degree of decomposition by acids than the publicly known erythromycin derivatives of the prior art. Thus, even if administered orally, the erythromycin derivatives of the present invention are little decomposed by gastric acid, in contrast to the publicly known erythromycin derivatives, and thus exhibited a strong enterokinesis stimulating activity.

We claim:
1. A compound represented by the formula:

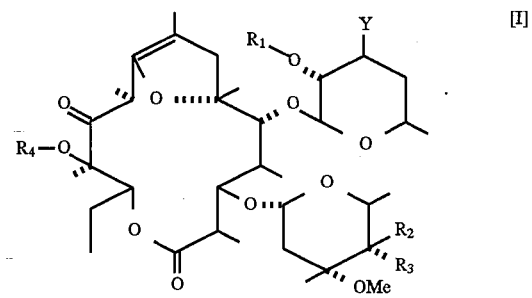

wherein $R_1$ is a hydrogen atom or an acyl group selected from the group consisting of a formyl group, an acetyl group, a propionyl group, a butyryl group, a pivaloyl group, a benzoyl group, an ethoxycarbonyl group, a t-butoxycarbonyl group, and a benzyloxycarbonyl group;

$R_2$ and $R_3$ may be the same or different, and each represents a hydrogen atom, a hydroxyl group, an amino group, or an acyloxy group selected from the group consisting of a formyloxy group, an acetyloxy group, a propionyloxy group, a butyryloxy group, a pivaloyloxy group, a benzoyloxy group, an ethoxycarbonyloxy group, a t-butoxycarbonyloxy group, and a benzyloxycarbonyloxy group, or, in combination, they represent =O or =$NOR_{10}$, where $R_{10}$ represents a hydrogen atom or a lower-alkyl group;

$R_4$ represents a hydrogen atom or a lower alkyl group; and

Y represents —$NR_5R_6$ or —$N^+R_7R_8R_9X$, where $R_5$, $R_6$, $R_7$, $R_8$ and $R_9$ may be the same or different, and each represents a hydrogen atom; an unsubstituted or substituted group selected from the group consisting of a lower alkyl group, a lower alkenyl group, and a lower alkynyl group, said substituents being selected from the group consisting of a hydroxy group, an amino group, a halogen atom, a cyano group, an alkyloxy group, a mercapto group, a carbamoyl group, and an acyl group selected from the group consisting of a formyl group, an acetyl group, a propionyl group, a butyryl group, a pivaloyl group, a benzoyl group, an ethoxycarbonyl group, a t-butoxycarbonyl group, and a benzyloxycarbonyl group; a cycloalkyl group of 3–8 carbon atoms; or a 3–7-membered heterocyclic group having an oxygen atom, nitrogen atom or sulphur atom as a heteroatom; said cycloalkyl and heterocyclic groups being unsubstituted or substituted by a group selected from the group consisting of a hydroxy group, an amino group, a halogen atom, a cyano group, an alkyloxy group, a mercapto group, a carbamoyl group, a lower alkyl group, a lower alkenyl group, a lower alkynyl group, an aryl group, an aralkyl group, and an acyl group selected from the group consisting of a formyl group, an acetyl group, a propionyl group, a butyryl group, a pivaloyl group, a benzoyl group, an ethoxycarbonyl group, a t-butoxycarbonyl group, and a benzyloxycarbonyl group; and X represents an anion selected from the group consisting of a chloride ion, a bromide ion, an iodide ion, a carboxylate ion, and a sulfonate ion; where $R_5$ and $R_6$, or $R_7$ and $R_8$ may form an azacycloalkyl group together with the neighboring nitrogen atom, respectively, said azocycloalkyl group being one obtained by replacing one or more carbon atoms of a cycloalkyl group of 3-8 carbon atoms by nitrogen atoms;

or a salt thereof.

2. A compound in accordance with claim 1, wherein said azocycloalkyl group has one nitrogen atom.

3. A compound in accordance with claim 1 wherein said azocycloalkyl group is selected from the group consisting of an aziridinyl group, an azetidinyl group, a pyrrolidinyl group, a piperidinyl group, and a hexamethyleneimino group.

4. A compound in accordance with claim 1, wherein said cycloalkyl group is selected from the group consisting of a cyclobutyl group, a cyclopentyl group, and a cyclohexyl group.

5. A compound in accordance with claim 1, wherein said 3-7-membered heterocyclic group is selected from the groups consisting of aziridine, azetidine, pyrrolidine, piperidine, oxirane, oxetane, oxolane, tetrahydropyran, thiirane, thietane, thiolane, and thiane.

6. A compound in accordance with claim 1, wherein said pharmaceutically acceptable salt comprises the salt of an acid selected from the group consisting of hydrochloric acid, hydrobromic acid, hydriodic acid, sulfuric acid, acetic acid, oxalic acid, maleic acid, fumaric acid, succenic acid, and methanesulfonic acid.

7. A compound in accordance with claim 1, wherein said compound is isopropyl-nor-12-O-methyl-11-oxo-8,9-anhydroethromycin A 6,9-hemiketal.

8. A compound in accordance with claim 1, wherein said compound is isopropyl-nor-12-O-methyl-11-oxo-8,9-anhydroethromycin A 6,9-hemiketal fumarate monohydrate.

9. A method for stimulating the contractile motility of an alimentary canal, comprising administering to a mammal in need of such stimulation an effective amount of a compound in accordance with claim 1.

10. A method in accordance with claim 9, wherein said administering step comprises oral administration.

11. A method in accordance with claim 9 for the treatment of dysfunction of enterokinetics in a patient, comprising administering to the patient an effective amount of said compound.

12. A method in accordance with claim 9 for the treatment of a gastrointestinal complaints due to hypokinesia in a patient, comprising administering to the patient an effective amount of said compound.

13. A compound represented by the formula:

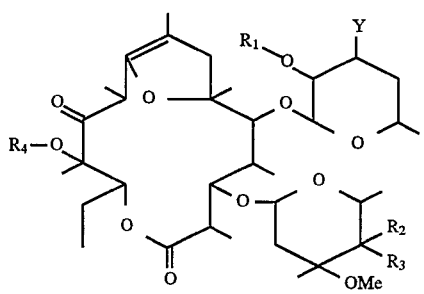

[I]

wherein $R_1$ is a hydrogen atom or an acyl group selected from the group consisting of a formyl group, an acetyl group, a propionyl group, a butyryl group, a pivaloyl group, a benzoyl group, an ethoxycarbonyl group, a t-butoxycarbonyl group, and a benzyloxycarbonyl group;

$R_2$ and $R_3$ may be the same or different, and each represents a hydrogen atom, a hydroxyl group, an amino group, or an acyloxy group selected from the group consisting of a formyloxy group, an acetyloxy group, a propionyloxy group, a butyryloxy group, a pivaloyloxy group, a benzoyloxy group, an ethoxycarbonyloxy group, a t-butoxycarbonyloxy group, and a benzyloxycarbonyloxy group, or, in combination, they represent =O or =NOR$_{10}$, where $R_{10}$ represents a hydrogen atom or a lower-alkyl group;

$R_4$ represents a hydrogen atom or a lower alkyl group; and y represents —NR$_5$R$_6$ or —N$^+$R$_7$R$_8$R$_9$X$^-$, where $R_5$, $R_6$, $R_7$, $R_8$ and $R_9$ may be the same or different, and each represents a hydrogen atom; an unsubstituted or substituted group selected from the group consisting of a lower alkyl group, a lower alkenyl group, and a lower alkynyl group, said substituents being selected from the group consisting of a hydroxy group, an amino group, a halogen atom, a cyano group, an alkyloxy group, a mercapto group, a carbamoyl group, and an acyl group selected from the group consisting of a formyl group, an acetyl group, a propionyl group, a butyryl group, a pivaloyl group, a benzoyl group, an ethoxycarbonyl group, a t-butoxycarbonyl group, and a benzyloxycarbonyl group; a cycloalkyl group of 3-8 carbon atoms; or a 3-7-membered heterocyclic group having an oxygen atom, nitrogen atom or sulphur atom as a heteroatom; said cycloalkyl and heterocyclic groups being unsubstituted or substituted by a group selected from the group consisting of a hydroxy group, an amino group, a halogen atom, a cyano group, an alkyloxy group, a mercapto group, a carbamoyl group, a lower alkyl group, a lower alkenyl group, a lower alkynyl group, an aryl group, an aralkyl group, and an acyl group selected from the group consisting of a formyl group, an acetyl group, a propionyl group, a butyryl group, a pivaloyl group, a benzoyl group, an ethoxycarbonyl group, a t-butoxycarbonyl group, and a benzyloxycarbonyl group; and X represents an onion selected from the group consisting of a chloride ion, a bromide ion, an iodide ion, a carboxylate ion, and a sulfonate ion; where $R_5$ and $R_6$, or $R_7$ and $R_8$ may form an azacycloalkyl group together with the neighboring nitrogen atom, respectively, said azacycloalkyl group being one obtained by replacing one or more carbon atoms of a cycloalkyl group of 3-8 carbon atoms by nitrogen atoms;

or a salt thereof.

14. A compound in accordance with claim 13, wherein said azocycloalkyl group has one nitrogen atom.

15. A compound in accordance with claim 13, wherein said azocycloalkyl group is selected from the group consisting of an aziridinyl group, an azetidinyl group, a pyrrolidinyl group, a piperidinyl group, and a hexamethyleneimino group.

16. A compound in accordance with claim 13, wherein said cycloalkyl group is selected from the group consisting of a cyclobutyl group, a cyclopentyl group, and a cyclohexyl group.

17. A compound in accordance with claim 13, wherein said 3-7-membered heterocyclic group is selected from the groups consisting of aziridine, azetidine, pyrrolidine, piperidine, oxirane, oxetane, oxolane, tetrahydropyran, thiirane, thietane, thiolane, and thiane.

18. A compound in accordance with claim 13, wherein said pharmaceutically acceptable salt comprises the salt of an acid selected from the group consisting of hydrochloric acid, hydrobromic acid, hydriodic acid, sulfuric acid, acetic acid, oxalic acid, maleic acid, fumaric acid, succinic acid, and methanesulfonic acid.

19. A method for stimulating the contractile motility of an alimentary canal, comprising administering to a mammal in need of such stimulation an effective amount of a compound in accordance with claim 13.

20. A method in accordance with claim 19, wherein said administering step comprises oral administration.

21. A method in accordance with claim 19, for the treatment of dysfunction of enterokinetics in a patient, comprising administering to the patient an effective amount of said compound.

22. A method in accordance with claim 19 for the treatment of a gastrointestinal complaints due to hypokinesia in a patient, comprising administering to the patient an effective amount of said compound.

* * * * *